US007348172B2

(12) United States Patent
Paloheimo et al.

(10) Patent No.: US 7,348,172 B2
(45) Date of Patent: Mar. 25, 2008

(54) METHOD AND DNA CONSTRUCTS FOR INCREASING THE PRODUCTION LEVEL OF CARBOHYDRATE DEGRADING ENZYMES IN FILAMENTOUS FUNGI

(75) Inventors: Marja Paloheimo, Vantaa (FI); Arja Mantyla, Helsinki (FI); Sanna Leskinen, Hanko (FI); Richard Fagerstrom, Espoo (FI); Jarno Kallio, Jarvenpaa (FI); Terhi Puranen, Nurmijarvi (FI); Raija Lantto, Klaukkala (FI); Pirkko Suominen, Maple Grove, MN (US)

(73) Assignee: AB Enzymes Oy, Rajamäki (FI)

( * ) Notice: Subject to any disclaimer, the term of this patent is extended or adjusted under 35 U.S.C. 154(b) by 0 days.

(21) Appl. No.: 11/108,163

(22) Filed: Apr. 18, 2005

(65) Prior Publication Data

US 2006/0014247 A1   Jan. 19, 2006

Related U.S. Application Data

(60) Provisional application No. 60/562,692, filed on Apr. 16, 2004.

(51) Int. Cl.
| | |
|---|---|
| *C12P 21/06* | (2006.01) |
| *C12N 9/88* | (2006.01) |
| *C12N 1/15* | (2006.01) |
| *C12N 15/70* | (2006.01) |
| *C12N 15/74* | (2006.01) |
| *C12Q 1/68* | (2006.01) |
| *C07H 21/04* | (2006.01) |

(52) U.S. Cl. .............. 435/200; 435/254.3; 435/254.11; 435/6; 435/69.1; 435/232; 435/320.1; 435/484; 536/23.2

(58) Field of Classification Search ............... 435/69.1, 435/232, 254.3, 484; 536/23.2
See application file for complete search history.

(56) References Cited

U.S. PATENT DOCUMENTS

| | | | |
|---|---|---|---|
| 5,306,633 | A | 4/1994 | Gottschalk et al. |
| 5,364,770 | A | 11/1994 | Berka et al. |
| 5,712,142 | A | 1/1998 | Adney et al. |
| 5,861,271 | A | 1/1999 | Fowler et al. |
| 5,935,836 | A | 8/1999 | Vehmaanperä et al. |
| 6,083,734 | A | 7/2000 | Chuang et al. |
| 6,300,114 | B1 | 10/2001 | Mäntylä et al. |
| 6,506,593 | B2 | 1/2003 | Mäntylä et al. |
| 6,562,340 | B1 | 5/2003 | Bedford et al. |
| 6,667,170 | B1 | 12/2003 | Mäntylä et al. |
| 2001/0024815 | A1* | 9/2001 | Mantyla et al. ............. 435/200 |
| 2003/0148453 | A1 | 8/2003 | Mäntylä et al. |

FOREIGN PATENT DOCUMENTS

| | | |
|---|---|---|
| EP | 1 344 820 A1 | 9/2003 |
| EP | 1 408 108 A2 | 4/2004 |
| WO | WO 90/15860 | 12/1990 |
| WO | WO 93/25693 | 12/1993 |
| WO | WO 94/21785 | 9/1994 |
| WO | WO 97/15660 A1 | 5/1997 |
| WO | WO 97/27306 | 7/1997 |
| WO | WO 01/96382 A2 | 12/2001 |
| WO | WO 02/057538 A2 | 7/2002 |

OTHER PUBLICATIONS

Kimura et al. Stable expression of a thermostable xylanase of *Chlostridium thermocellum* in cultured tobacco cells, J Bioscience & BioEngineering, 95(4): 397-400, 2003.*
Aho, S., et al., "Monoclonal antibodies against core and cellulose-binding domains of *Trichoderma reesei* cellobiohydrolases I and II and endoglucanase I," *Eur. J. Biochem. 200*:643-649, Blackwell Science Ltd. (1991).
Alcocer, M., et al., "Comparison of modular and non-modular xylanases as carrier proteins for the efficient secretion of heterologous proteins from *Penicillium funiculosum*," *Appl. Microbio. Biotechnol. 60*:726-732, Springer-Verlag (2003; available online Dec. 21, 2002).
Araki, R., et al., "Essential role of the family-22 carbohydrate-binding modules for β-1, 3-1, 4-glucanase activity of *Clostridium stercorarium* Xyn10B," *FEBS Letters 561*:155-158, Federation of European Biochemical Societies (2004; available online Feb. 20, 2004).
Bailey, M.J., et al., "Induction, isolation and testing of stable *Trichoderma reesei* mutants with improved production of solubilizing cellulase," *Enzyme Microb. Technol. 3*:153-157, Elsevier Science (1981).
Bailey, M.J., et al., "Interlaboratory testing of methods for assay of xylanase activity," *J. Biotechnol. 23*:257-270, Elsevier Science Publishers (1992).

(Continued)

*Primary Examiner*—Rebecca E. Prouty
*Assistant Examiner*—Iqbal Chowdhury
(74) *Attorney, Agent, or Firm*—Sterne, Kessler, Goldstein & Fox P.L.L.C.

(57) ABSTRACT

The invention is related to a method and DNA constructs for obtaining in a filamentous fungus host a higher production level of a carbohydrate degrading (CD) enzyme, having in its original state a catalytic module (CAT) and a carbohydrate binding module (CBM) separated by a linker region. The DNA construct comprising a truncated actinomycetes, preferably *Nonomuraea flexuosa* (NJ) derived DNA sequence encoding a truncated form of the CD enzyme, for example Nf Xyn11A, Nf Xyn10A, and is introduced into a filamentous fungal host. Said CD enzyme contains the catalytically active region of CAT but lacks part or all of the CBM, or all of the CBM and part or all of the linker region and is expressed and secreted under the control of regulatory sequences comprising at least a signal sequence, but also promoters, terminators and DNA sequences encoding a secretable carrier protein or domains thereof, preferably originating from filamentous fungi are included. The production level obtained with DNA sequence having the shortened DNA sequence encoding the truncated form of the CD enzyme is higher than the production level obtained with DNA construct encoding the corresponding full length CD enzyme.

32 Claims, 12 Drawing Sheets

OTHER PUBLICATIONS

Figure 3:
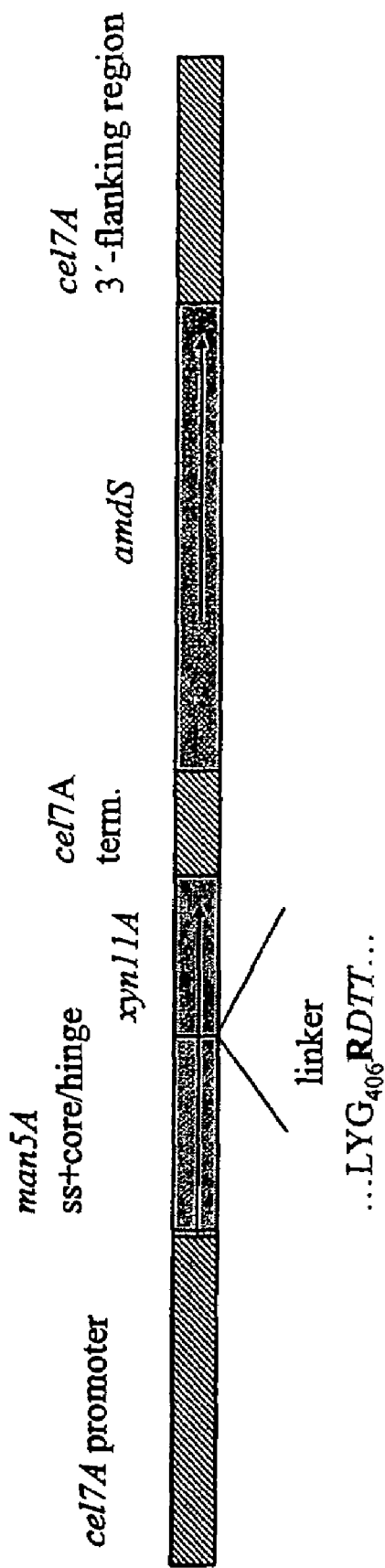

Benson, S., "A Rapid Procedure for Isolation of DNA Fragments from Agarose Gels," *Biotechniques* 2:66-68, Eaton Publishing Company (1984).

Calmels, T.P.G., et al., "Proteolytic events in the processing of secreted proteins in fungi," *J. Biotechnol.* 17:51-66, Elsevier Science Publishers (1991).

Drocourt, D., et al., "Cassettes of the *Streptoalloteichus hindustanus ble* gene for transformation of lower and higher eukaryotes to phleomycin resistance," *Nucleic Acids Res.* 18: 4009, Oxford University Press (1990).

Fagerström, R., et al., "Characterization, subsite mapping and partial amino acid sequence of glucoamylase from the filamentous fungus *Trichoderma reesei*," *Biotechnol. Appl. Biochem.* 21:223-231, Portland Press (1995).

Fujimoto, Z., et al., "Crystal Structure of *Streptomyces olivaceoviridis* E-86 β-Xylanase Containing Xylan-binding Domain," *J. Mol. Biol.* 300:575-585, Academic Press (2000).

Gilkes, N.R., et al., "Structural and functional relationships in two families of beta-1,4-glycanases," *Eur. J. Biochem.* 202:367-377, Blackwell Science Ltd. (1991).

Gouka, R., et al., "Efficient production of secreted proteins by *Aspergillus*: progress, limitations and prospects," *Appl. Microbiol. Biotechnol.* 47:1-11, Springer-Verlag (1997).

Greiner-Mai, E., et al,. "Morphological and Biochemical Characterization and Emended Descriptions of Thermophilic Actinomycetes Species," *Syst. Appl. Microbiol.*, 9:97-109, G. Fischer Verlag (1987).

Gritz, L., et al., "Plasmid-encoded hygromycin B resistance: the sequence of hygromycin B phosphotransferase gene and its expression in *Escherichia coli* and *Saccharomyces cerevisiae,*" *Gene* 25:179-188, Elsevier/North-Holland (1983).

Hirabayashi, J., et al., "Novel Galactose-binding Proteins in Annelida. Characterization of 29-kDa tandem repeat-type lectins from the earthworm *Lumbricus terrestris,*" *J. Biol. Chem.* 273:14450-14460, The American Society for Biochemistry and Molecular Biology, Inc. (1998).

Holtz, C., et al., "Production and properties of xylanases from thermophilic actinomycetes," *Antonie van Leeuwenhoek* 59:1-7, Kluwer Academic Publishers (1991).

Jeenes, D., et al., "Heterologous Protein Production by Filamentous Fungi," *Biotechnol. Genet. Eng. Rev.* 9:327-367, Intercept (1991).

Joutsjoki, V., et al., "Transformation of *Trichoderma reesei* with the *Hormoconis resinae* glucoamylase P (gamP) gene: production of a heterologous glucoamylase by *Trichoderma reesei,*" *Curr. Genet.* 24:223-228, Springer International (1993).

Kalkkinen, N., and Tilgmann, C., "A Gas-Pulsed-Liquid-Phase Sequencer Constructed from a Beckman 890D Instrument by Using Applied Biosystems Delivery and Cartridge Blocks," *J. Protein Chem.* 7:242-243, Kluwer Academic/Plenum Publishers (1988).

Karhunen, T., et al., "High frequency one-step gene replacement in *Trichoderma reesei*. I. Endoglucanase I overproduction," *Mol. Gen. Genet.* 241:515-522, Springer-Verlag (1993).

Kelly, J.M, and Hynes, M.J., "Transformation of *Aspergillus niger* by the *amdS* gene of *Aspergillus nidulans,*" *EMBO J* 4:475-479, Oxford University Press (1985).

Lowry, O.H., et al., "Protein Measurement With The Folin Phenol Reagent," *J. Biol. Chem.* 193:265-275, American Society for Biochemistry and Molecular Biology (1951).

Mach, R., et al., "Transformation of *Trichoderma reesei* based on hygromycin B resistance using homologous expression signals," *Curr. Genet.* 25:567-570, Springer International (1994).

Matheucci, Jr., E., et al., "Structure, organization and promoter expression of the actin-encoding gene in *Trichoderma reesei,*" *Gene* 161:103-106, Elsevier/North-Holland (1995).

Paloheimo, M., et al., "High-Yield Production of a Bacterial Xylanase in the Filamentous Fungus *Trichoderma reesei* Requires a Carrier Polypeptide with an Intact Domain Structure," *Appl. Environ. Microbiol.* 69:7073-7082, American Society For Microbiology (Dec. 2003).

Penttilä, M., et al., "Homology between cellulase genes of *Trichoderma reesei*: complete nucleotide sequence of the endoglucanase I gene," *Gene* 45:253-263, Elsevier/North Holland (1986).

Penttilä, M., et al., "A versatile transformation system for the cellulolytic filamentous fungus *Trichoderma reesei,*" *Gene* 61:155-164, Elsevier/North Holland (1987).

Pfabigan, N., et al., "Prebleaching of kraft pulp with full-length and truncated forms of a thermostable modular xylanase from *Rhodothermus marinus,*" *Biotechnol. Lett.* 24:1191-1197, Kluwer Academic Publishers (2002).

Raeder, U., et al., "Rapid preparation of DNA from filamentous fungi," *Lett. Appl. Microbiol.* 1:17-20, Blackwell Scientific Publications (1985).

Rixon, J.E., et al., "Do the non-catalytic polysaccharide-binding domains and linker regions enhance the biobleaching properties of modular xylanases?" *Appl. Microbiol. Biotechnol.* 46:514-520, Springer-Verlag (1996).

Saloheimo, M., et al., "EGIII, a new endoglucanase from *Trichoderma reesei*: the characterization of both gene and enzyme," *Gene* 63:11-21, Elsevier/North-Holland (1988).

Stålbrand, H., et al., "Cloning and Expression in *Saccharomyces cerevisiae* of a *Trichoderma reesei* β-Mannanase Gene Containing a Cellulose Binding Domain," *Appl. Environ. Microbiol.* 61:1090-1097, American Society for Microbiology (1995).

Suominen, P., et al., "High frequency one-step gene replacement in *Trichoderma reesei*. II. Effects of deletions of individual cellulase genes," *Mol. Gen. Genet.* 241:523-530, Springer Verlag (1993).

Teeri, T.T., et al., "Domain function in *Trichoderma reesei* cellobiohydrolases," *J. Biotechnol.* 24:169-176, Elsevier Science Publishers (1992).

Teeri, T.T., et al., "Homologous domains in *Trichoderma reesei* cellulolytic enzymes: gene sequence and expression of cellobiohydrolase II," *Gene* 51:43-52, Elsevier Science Publishers (1987).

Tomme, P., et al., "Cellulose-Binding Domains: Classification and Properties," in: *Enzymatic Degradation of Insoluble Carbohydrates*, American Chemical Society, 142-163 (1995).

Törrönen, A., et al., "The Two Major Xylanases From *Trichoderma reesei*: Characterization of Both Enzymes and Genes," *Biotechnol.* 10:1461-1465, Butterworth-Heinemann (1992).

van den Hondel, C.A.M.J.J., et al., "Heterologous Gene Expression in Filamentous Fungi," in *More Gene Manipulations in Fungi*, Bennet, J.W., and Lasure, L.L., eds., Academic Press, San Diego, CA, pp. 396-428 (1991).

Finnish Search Report for Patent Application No. FI 20040551, performed on Oct. 22, 2004, Helsinki, Finland.

International Search Report for Patent Application No. PCT/FI2005/050123, mailed Jun. 23, 2005, International Searching Authority, Helsinki, Finland.

Paloheimo, M., et al., "Increased Production of Xylanase by Expression of a Turncated Version of the *xyn11A* Gene from *Nonomuraea flexuosa* in *Trichoderma reesei,*" *Appl. Environ. Microbiol.* 73:3215-3224, American Society for Microbiology (May 2007).

Leskinen, S., et al., "Thermostable xylanases, Xyn10A and Xyn11A, from the actinomycete *Nonomuraea flexuosa*: isolation of the genes and characterization of recombinant Xyn11A polypeptides produced in *Trichoderma reesei,*" *Appl. Microbiol. Biotechnol* 67:495-505 Springer-Verlag (Jan. 2005).

Black, G.W., et al., "Cellulose binding domains and linker sequences potentiate the activity of hemicellulases against complex substrates," *J. Biotechnol.* 57:59-69, Elsevier Science Publishers (1997).

Haakana, H., et al., "Cloning of cellulase genes from *Melanocarpus albomyces* and their efficient expression in *Trichoderma reesei*," *Enzyme Microb. Technol.* 34:159-167, Elsevier Science (Feb. 2004).

Supplementary European Search Report for European Application No. EP 05 73 5322, Munich, Germany, mailed on Oct. 24, 2007.

\* cited by examiner

FIG. 1

```
   1 ttcggcagcctattgacaaatttcgtgaatgttcccacacttgctctgcagacggcccgcgatcatgggtgcacgtcggcgggaccggtgctgctccga
 101 cgccattcggggtgtgcgcctgcgggcgcgtcgatccgcgggactcccgcggttccttccgtccctctaatgaggctcaggcATGGGCG
                                                                                        m g v
 201 TGAACGCCTTCCCAGACCGGAGCTCGGCGTTCACCGGGCTGTACCGGGCGGGGCCTGTACCGGCCCTGGCCGTGAGCGTGGTCGGTGTCACGGCCCT
   4  n a f p r p g a r f t g g l y r a l a a a t v s v v g v v t a l 301 GACGGTGACCCAGCCCGCCAGCGCCGCGAGCACGCTCGCCGAGGGTGCCGCAGCACAACCGTACTTCGGCGTGGCCATCGCCGAGAACAGGCTC
  37  t v t q p a a a  A A S T L A E G A A Q H N R Y F G V A I A A N R L
                                                                #1696                  #1697

401 AACGACTCGGTCTACACCAACATCGCGAACCGCGAGTTCAACTCGGTGACGGCCGAGAACGAGATGAAGATCGACGCCACCGAGCCGCAGCAGGGGCGT
  70  N D S V Y T N I A N R E F N S V T A E N E M K I D A T E P P Q Q G R F
       #1698                         #1704

501 TCGACTTCACCCAGGCCGACCGGATCTACAACTGGGCGCGGCAGAACGGCAAGCAGGTCCGCGGCCACACCCTGGCCTGGCACTCGCAGCCGCAGTG
 104  D F T Q A D R I Y N W A R Q N G K Q V R G H T L A W H S Q Q P Q W

601 GATGCAGAACCTCAGCGGCCAGGCGCTGCGCCAGGCGATGATCAACCACATCCAGGGGGTCATGTCCTACTACCGGGGCAAGATCCCGATCTGGGACGTG
 137  M Q N L S G Q A L R Q A M I N H I Q G V M S Y Y R G K I P I W D V

701 GTGAACGAGGCGTTCGAGGACGGCAACAGCGGCCGCCGCCGCGACTCCAACCTCCAGCGCACCGGTAACGACTGGATCGAGGTCGCGTTCCGCACCGCC
 170  V N E A F E D G N S G R R R D S N L Q R T G N D W I E V A F R T A R

801 GCCAGGCGGACCCCTCGGCCAAGCTCTGCTACAACGACTACAACATCGAGAACTGGAACGCCAAGACCCAGGCGGTCTACAACATGGTGCGGGACTT
 204  Q A D P S A K L C Y N D Y N I E N W N A A K T Q A V Y N M V R D F

901 CAAGTCCCGCGGCGTGCCCATCGACTGCGTGGGCTTCCAGTCGCACTTCAACAGCGGTAACCCGTACAACCCGAACTTCCGCACCACCCTGCAGCAGTTC
 237  K S R G V P I D C V G F Q S H F N S G N P Y N P N F R T T L Q Q F

1001 GCGGGCCCTCGGCGGTCGAGGTCACCGAGCTGGACATCGAGAACGCCCCGGCCCAGACCTACGCCAGCGTGATCCGGGACTGCCTCGCCGTGACC
 270  A A L G V D V E V T E L D I E N A P A Q T Y A S V I R D C L A V D R
```

FIG. 2A

```
1101 GCTGCACCGGCGATCACCGGTCTCGGGGTGTCCGGCGACAGCGACTCCTGGCGCTCGTACCAGAACCCGCTGCTGTTCGACAACAACGGCAACAAGAAGCAGGC
 304  C  T  G  I  T  V  W  G  V  R  D  S  D  S  W  R  S  Y  Q  N  P  L  L  F  D  N  N  G  N  K  K  Q  A
      #1699

1201 CTACTACGCGGTGCTCGACGCCCTGAACGAGGGCTCCGACGACGGTGGCGGCCCGTCCAACCCGGTCTCGCCGCCGGGTGGCGGTCTCGGCGGTGGCGGTTCCGGGCAG
 337  Y  Y  Y  A  V  L  D  A  L  N  E  G  S  D  D  G  G  G  P  S  N  P  P  V  S  P  P  P  G  G  G  S  G  Q
                                                linker 1301 ATCCGGGGCGTGGCTTCCAACCGGTGCATCGACGTTCCAACACCGCCGACGGCAACGGCAACACCGCCGACGGCACCCAGGTCCAGCTGTACGACTGCCACAGCGGTTCCAACC
 370  I  R  G  V  A  S  N  R  C  I  D  V  P  N  G  N  T  A  D  G  T  Q  V  Q  L  Y  D  C  H  S  G  S  N  Q
                                         α-subdomain 1401 AGCAGTGGACCTACACCTCGTCCGGTGAGTTCCGCATCTTCGGCAACAAGTGCCTCGACGCGGGCGGCTCCAACGGTGCGGTGGTCCAGATCTACAG
 404  Q  W  T  Y  T  S  S  G  E  F  R  I  F  G  N  K  C  L  D  A  G  G  S  S  N  G  A  V  V  Q  I  Y  S
                                         ß-subdomain 1501 CTGCTGGGGCGGCGCCAACCAGAAGTGGGAGCTCCGGGCCGACGGCACCATCGTGGGCGTGCAGTCCGGGCTGTGCCTCGACGCGGTGGGTGGCGGCACC
 437  C  W  G  G  A  N  Q  K  W  E  L  R  A  D  G  T  I  V  G  V  Q  S  G  L  C  L  D  A  V  G  G  T
                                                                                γ-subdomain 1601 GGCAACGGCACGCGGCTGCAGCTCTACTCCTGCTGGGGCGGCAACAACCAGAAGTGGTCCTACAACGCCTGAtcccggctgatcgaccctagttgaggc
 470  G  N  G  T  R  L  Q  L  Y  S  C  W  G  G  N  N  Q  K  W  S  Y  N  A  *        492

1701 cgcctccggtacggcaccgcgcgtaccggaggcggtcccttgttcgtccaggacggaaggacggtctgagcaggcgatcggcggcgatcgggcaccatggtgggca
1801 ggcacgaaagcggagggagggggtcgcatgccgcgagtccggagtgttcctccacctga        1864
```

FIG. 2B

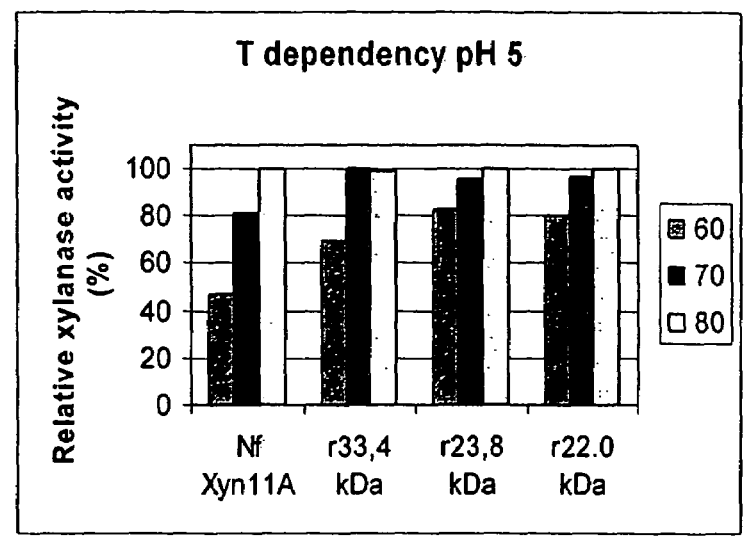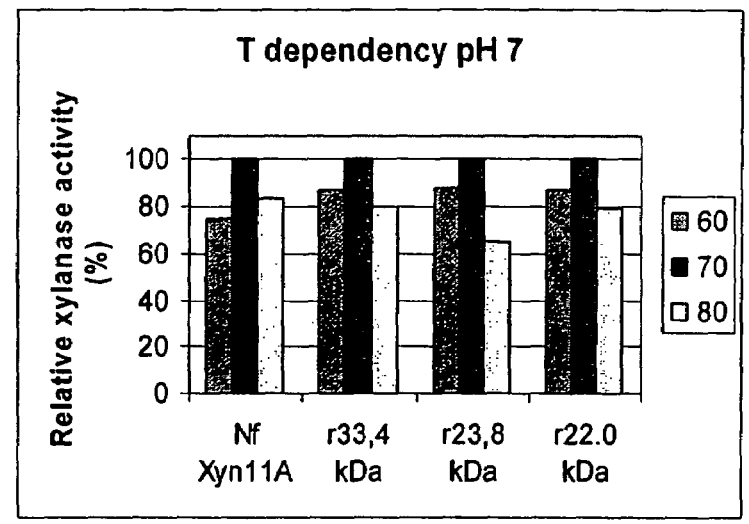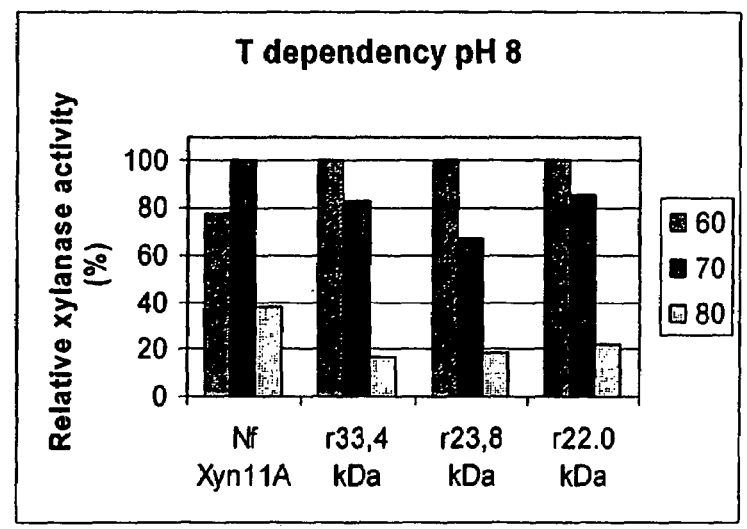
FIG. 5

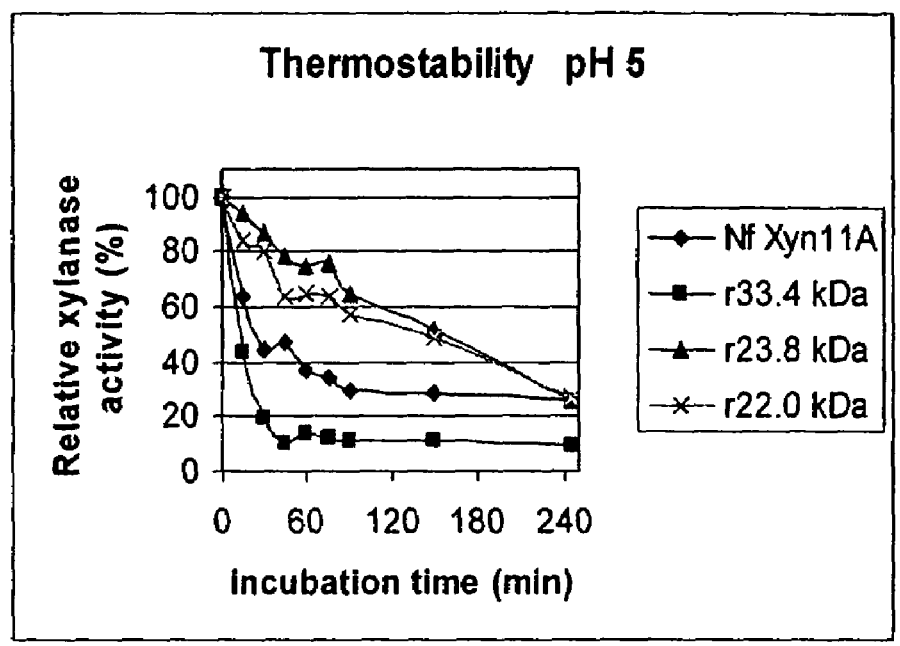
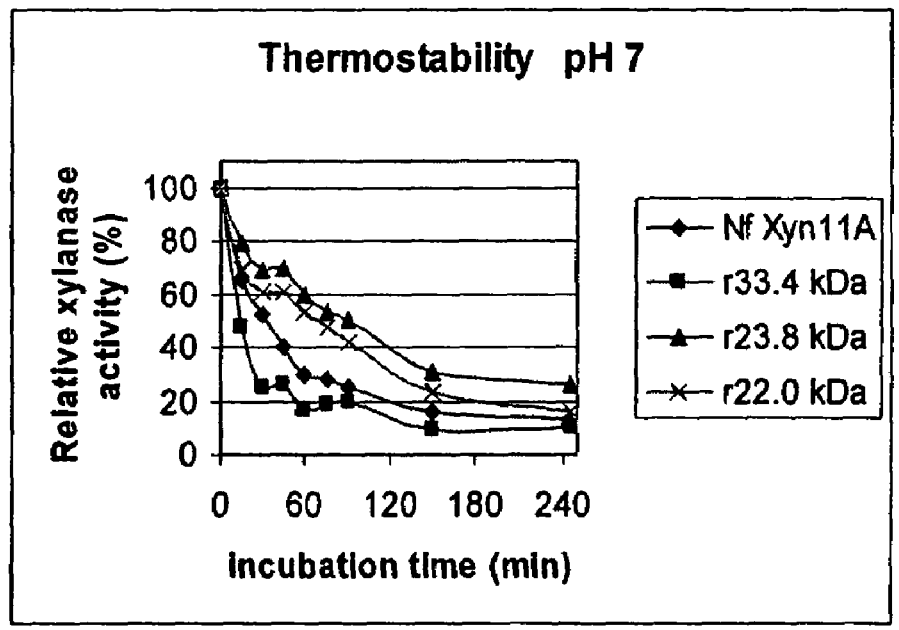
FIG. 6

METHOD AND DNA CONSTRUCTS FOR INCREASING THE PRODUCTION LEVEL OF CARBOHYDRATE DEGRADING ENZYMES IN FILAMENTOUS FUNGI

CROSS REFERENCE TO RELATED APPLICATIONS

This application claims the benefit of U.S. Provisional Application No. 60/562,692, filed Apr. 16, 2004, the contents of which are incorporated herein by reference.

BACKGROUND OF THE INVENTION

1. Field of the Invention

The present invention is related to molecular biology and particularly to methods and DNA constructs for increasing the production level in a filamentous fungal host when producing carbohydrate degrading (CD) enzymes, which in their native, unmodified state have a catalytic module (CAT) and a carbohydrate binding module (CBM) separated by a linker region. Carbohydrate degrading enzymes with the structure defined above are found among filamentous fungi and bacteria, such as strains of actinomycete, including *Nonomuraea flexuosa* Xyn11A or Xyn10A. For high yield production, a shortened DNA sequence, which encodes a truncated form of the desired carbohydrate degrading enzymes, is used.

2. Background Art

Plant cell walls consist mainly of a complex mixture of polysaccharides, primarily cellulose, lignin and hemicellulose. In most plant material, xylan is the major hemicellulose component, consisting of a main chain of 1,4-linked beta-D-xylopyranosyl residues that often carry acetyl, arabinosyl and glucuronosyl substituents. Carbohydrate degrading enzymes are useful as feed additives, because of their beneficial effects on the adsorption of feed components and in prebleaching of kraft pulp, wherein they are used as simple and cost-effective alternatives to toxic chlorine-containing chemicals. The main enzyme needed to enhance the delignification of kraft pulp is endo-β-1,4-xylanase (EC 3.2.1.8), but the presence of other enzymes such as mannanase, lipase, and α-galactosidase have been shown to improve the effect of enzymatic treatment. In enzyme-aided bleaching, pretreatment with xylanase removes xylan while preserving the cellulose content. Thereby, the need of bleaching chemicals is decreased and/or the brightness of the paper is increased. In feed applications, the beneficial effects obtained after enzyme addition, including increased growth rate and feed efficiency, result from the reduction of intestinal viscosity and release of nutrients from grain endosperm and aleurone layers.

The use of enzymatic treatments in both feed and pulp and paper industry has dramatically increased. As a corollary, the demand of carbohydrate degrading enzymes has also increased. This puts a pressure on the development of new efficient and cost-effective methods for the production of sufficient amounts of carbohydrate degrading enzymes having properties suitable for use in said industries. Xylanases that are active and stable at high temperature and alkaline pH are especially desirable in many industrial processes, due to the high temperatures and the alkaline conditions used in bleaching as well as the high temperatures used in downstream processing, e.g. pelleting.

Actinomycetes strains are known to produce thermostable enzymes with alkaline optima. Especially, thermophilic actinomycetes strains are a useful source of xylanases for industrial processes. Their activities and stability at high temperature are adequate for bleaching processes and other applications in which it is beneficial to perform the enzyme treatment at high temperatures. Useful genes have been cloned from e.g. *Thermomonospora fusca*, *Nonomuraea flexuosa* DSM43186, previously named as *Actinomadura flexuosa* or *Microtetraspora flexuosa* as well as from some *Streptomyces* species. The cloning of two *Nonomuraea flexuosa* xylanases has been described in U.S. Pat. Nos. 5,935,836, 6,300,114, 6,506,593 and 6,667,170.

The desired high temperature resistant carbohydrate degrading enzymes with extreme pH optima originate from relatively unstudied bacteria.

Typically, they have low production levels and are unsuitable for industrial production in large scale. Little or practically no experience exists about fermentation of said bacteria. Accordingly, transfer of a gene originating from said microbes, and encoding the desired enzyme, into a heterologous host organism is a feasible alternative for producing the desired enzyme.

Bacterial enzymes have been produced in bacterial hosts and yeasts, as disclosed, for example, in U.S. Pat. Nos. 5,306,633 and 5,712,142. U.S. Pat. No. 5,712,142 describes a method for increasing the thermostability of a bacterial cellulase from *Acidothermus cellulyticus* either by proteolytic cleavage or by expressing a shortened or truncated form of the gene encoding the full size cellulase in the yeast host, *Pichia pastoris*. WO 0196382 A2 describes a method for increasing the thermostability of *Rhodothermus marinus* cellulase by expressing a truncated form of the gene in *Escherichia coli*. Accordingly, several bacterial carbohydrate degrading enzymes have been described and it is known how to improve their thermostability.

Truncation of a multidomain xylanase from the anaerobic fungus *Neocallimastix patriciarum* was shown to improve the expression in *E. coli*, as disclosed in WO 9325693 A1.

Filamentous fungi, including *Aspergillus*, *Trichoderma*, and *Penicillium*, are known as effective producers of homologous and heterologous proteins. They are by far the most preferred host organisms for large scale production of industrial enzymes, including bulk production of amylases, glucoamylases, cellulases, xylanases, etc. The first attempts to produce bacterial enzymes in filamentous fungi were discouraging. The yields of the bacterial enzymes were low, not exceeding a few tens of milligrams per liter. In many of the reports, the enzymes were detected only intracellularly (Jeenes, et al., Biotechnol. Genet. Eng. Rev., 9, 327-367, 1991; van den Hondel, et al., In J. W. Bennet and L. L. Lasure (ed.) More genetic manipulations in fungi: Academic Press, San Diego, Calif.).

Genetic fusion strategies have been developed and used in order to improve yields of heterologous proteins in filamentous fungi as disclosed in U.S. Pat. No. 5,364,770 and WO 94/21785 and reviewed by Gouka et al., Appl. Microbiol. Biotechnol., 47, 1-11, 1997. Production of bacterial carbohydrate degrading enzymes from filamentous fungi, using gene fusions comprising a DNA sequence encoding a complete or a partial filamentous fingus secretable protein (polypeptide) as a carrier protein has been described in WO 97/27306 and US 2003/0148453. Using expression cassettes disclosed in said patent applications and comprising DNA sequences encoding a bacterial carbohydrate degrading enzyme fused in frame with a complete or partial filamentous fungus secretable protein, Paloheimo, et al., (Appl. Environ. Microbiol., 69, 7073-7082, 2003) have demonstrated that the production levels are remarkably increased when the gene encoding the bacterial enzyme is fused in frame with a filamentous fungal secretable polypeptide having an intact domain structure.

The objective of the present invention is to further improve the production levels of carbohydrate degrading enzymes, particularly, bacterial enzymes produced by recombinant DNA techniques from filamentous fungal hosts.

BRIEF SUMMARY OF THE INVENTION

The invention is related to a method and DNA constructs for improving the production levels of carbohydrate degrading enzymes using recombinant DNA techniques and filamentous fungi as hosts.

The carbohydrate degrading enzymes (CD) of the present invention are active on carbohydrate substrates and are such enzymes, wherein the complete enzyme in its original (native or unmodified) state has three characteristic domains or regions, which are a catalytic module (CAT) containing the active site and a carbohydrate binding module (CBM), which modules are separated by a linker region. Some carbohydrate binding modules, such as the carbohydrate binding module of AM50 (Nf Xyn10A) may have more than one sub-domain.

The method for obtaining the increased production level comprises a first step, wherein a DNA construct is designed. The DNA construct, which is introduced into a filamentous fungus host comprises regulatory sequences and a shortened DNA sequence encoding a truncated form of the desired carbohydrate degrading enzyme, which comprises the catalytically active region of CAT and lacks the CBM module or part of it, or all of the CBM and part or all of the linker region. The regulatory sequences are preferably derived from filamentous fungi and comprise at least one signal sequence.

The DNA sequence encoding the truncated form of the carbohydrate degrading enzyme originates from a bacterial strain, which may be an actinomycetes strain, as exemplified by Nonomuraea. Xylanases from Nonomuraea flexuosa, particularly, the thermostable xylanases Nf Xyn11A and Nf Xyn10A, are examples of carbohydrate degrading enzymes, the yields of which may be increased by applying recombinant DNA techniques and shortened DNA sequences encoding the truncated target carbohydrate degrading enzyme, which lacks part or all of the CBM, or all of the CBM and part or all of the linker region.

Such DNA sequences may be natural sequences isolated from bacterial genomes. They may be synthetic sequences prepared by known methods, such as PCR. Synthetic sequences include the codon optimized DNA sequences, in which the nucleotide codons of natural bacterial DNA sequences are modified to resemble the codon usage in the filamentous fungus host. The truncated forms of the carbohydrate degrading enzyme encoded by such codon optimized sequences have the catalytic activity corresponding to the enzyme encoded by a natural DNA sequence.

The truncated form of said carbohydrate degrading enzyme is expressed under the control of regulatory sequences originating from the same or different filamentous fungi. The regulatory sequences comprise at least a signal sequence derived from a filamentous fungus. The yield can be even more improved when the carbohydrate degrading enzyme described above is expressed under the control of regulatory sequences consisting of promoter sequences, terminator sequences, and particularly, DNA sequences encoding a carrier protein (polypeptide) including a signal sequence. The regulatory sequences may be obtained from the same or different filamentous fungi and combined in arbitrary ways. This means that the origin of the regulatory sequences and their order may vary.

The DNA sequences encoding the carrier protein may either include the whole coding region of the mature secretable carbohydrate degrading protein or a selected region or domain thereof which in its native secretable form consists of the N-terminal catalytic module (CAT) and a C-terminal carbohydrate binding domain (CBD) separated by a linker (hinge) region. The carrier protein may include the catalytic module (CAT), or the catalytic module (CAT) and part or all of the linker (hinge) region, or the catalytic module (CAT) and all of the linker (hinge) region and part or all of the carbohydrate binding domain (CBD). T. reesei Man5A core region or Man5A core/hinge region (Stålbrand et al., Appl. Environ. Microbiol., 61: 1090-1097, 1995) are examples of such carrier proteins.

The secretable carbohydrate degrading protein may include only the catalytic domain (CAT) which can be used as a carrier polypeptide. T. reesei, XYNI and XYNII are examples of such proteins (Törrönen et al., Biotechnol., 10:1461-1465, 1992). Some secretable proteins have their CBD in the N-terminal end of the enzyme. Example of such an enzyme is T. reesei Cel6A (CBHII) (Teeri et al., Gene, 51:43-52, 1987). A Cel6A CBD consists of an A, an A+B or an A+B+B' regions, wherein A is a carbohydrate binding domain, B is a hinge (linker) region, and B' is a duplicated hinge (linker) region. These regions can be used alone or in different combinations as possible carrier polypeptides.

Signal sequences may be selected from various secretable filamentous fungal polypeptides, especially Trichoderma and Aspergillus signal sequences, including the Man5A signal sequence (Stålbrand et al., Appl. Environ. Microbiol., 61:1090-1097, 1995) and the Cel6A signal sequence (Teeri et al., Gene, 51:43-52, 1987).

Promoter sequences may be selected from various filamentous fungal promoters, especially from Trichoderma and Aspergillus promoters, including a strong Trichoderma cel7A (cbh1) promoter. Terminator sequences are also obtainable from filamentous fungi, especially preferred is a Trichoderma cel7A terminator sequence.

When the shortened DNA sequence is a shortened Nf xyn11A (am24 (SEQ ID NO: 3) or am24* (SEQ ID NO: 5)) expressed and secreted solely under the control of a promoter and signal sequence originating from a filamentous fungi without any carrier protein or domains thereof, the production level of the truncated Nf Xyn11A is at least 2 times higher in shake flasks and often more than 8-10 times higher in a fermentation cultivation than the production level obtained when the corresponding full length Nf xyn11A is expressed and secreted under the control of the same promoter and signal sequence without a carrier protein or parts thereof.

When the shortened DNA sequence is a shortened Nf xyn11A (am24 (SEQ ID NO: 3) or am24* (SEQ ID NO: 5)) expressed and secreted under the control of a promoter, signal sequence and a DNA sequence encoding a carrier protein (polypeptide) or domains thereof, all regulatory sequences originating from filamentous fungi, the production level of the truncated Nf Xyn11A is at least two times higher (in shake flasks) than with a DNA sequence encoding the corresponding full length Nf Xyn11A expressed and secreted under the control of the same promoter, signal and carrier protein sequence or domains thereof. Even higher production levels are obtained in fermentation cultivations. It is to be noted that a further improvement was still achieved when a DNA sequence encoding a truncated bacterial enzyme was used, even if an improved production level was already known to be achieved, when DNA sequences encoding a full length bacterial enzyme, were expressed and secreted under the control of intact domains of filamentous fungal secretable carrier protein (Paloheimo, et al., Appl. Environ. Microbiol., 69, 7073-7082, 2003).

The feasibility of the present invention is demonstrated using the sequences listed below.

SEQ ID NO:1 Nf xyn11A nucleotide sequence (AJ508952), the coding region is from nt 303 to nt 1337. The GenBank sequence AJ508952 will show any revisions made to the sequence.

SEQ ID NO:2 am35 nucleotide sequence, Nf xyn11A coding region for the mature Nf Xyn11A (AM35) protein SEQ ID NO:3 am24 nucleotide sequence, shortened form of am35, includes a STOP codon SEQ ID NO:4 am35* nucleotide sequence, like am35 but 9 codons are changed in the sequence (Example 10) (the changes do not alter the encoded amino acid sequence)

SEQ ID NO:5 am24* nucleotide sequence, like am24 but 9 codons are changed in the sequence like in am35 * (Example 10)

SEQ ID NO:6 Nf xyn10A nucleotide sequence (AJ508953), coding region is from nt 194 to nt 1672. The GenBank sequence AJ508953 will show any revisions made to the sequence.

SEQ ID NO:7 am50 nucleotide sequence, Nf xyn10A coding region for the mature Nf Xyn10A (AM50) protein SEQ ID NO:8 The nucleotide sequence encoding the AM50 core and linker regions, includes a STOP codon SEQ ID NO:9 The nucleotide sequence encoding the AM50 core region, includes a STOP codon SEQ ID NO:10 Nf Xyn11A amino acid sequence (AJ508952) encoded by the Nf xyn11A gene. The GenBank sequence AJ508952 will show any revisions made to the sequence.

SEQ ID NO:11 r33.4 kDa=AM35=amino acid sequence for the full length mature Nf Xyn11A protein encoded by am35 and am35* genes SEQ ID NO:12 AM24, amino acid sequence for the truncated form from AM35 encoded by am24 and am24* genes SEQ ID NO:13 r23.8 kDa, amino acid sequence for the truncated form from AM35

SEQ ID NO:14 r22.0 kDa, amino acid sequence for the truncated form from AM35

SEQ ID NO:15 Nf Xyn10A, the amino acid sequence (AJ508953) encoded by the Nf xyn10A gene. The GenBank sequence AJ508953 will show any revisions made to the sequence.

SEQ ID NO:16 AM50, amino acid sequence for the full length mature Nf Xyn10A

SEQ ID NO:17 AM50 core+linker, amino acid sequence for the truncated form from AM50

SEQ ID NO:18 AM50 core, amino acid sequence for the truncated form from AM50

SEQ ID NO:19 AM50 core+linker+α/β domains of the tail, amino acid sequence for the truncated form from AM50

SEQ ID NO:20 AM50 core+linker+α domain of the tail, amino acid sequence for the truncated form from AM50

SEQ ID NO:21 Amino acid sequence for the synthetic linker sequence coding for a Kex2-like protease cleavage signal Lys-Arg included in all the constructs to ensure cleavage of the fusion protein.

SEQ ID NO:22 An additional amino acid sequence preceding the Kex2 site in the expression cassette pALK1264, pALK1131 and pALK1134.

SEQ ID NO:23 The N-terminal amino acid sequence of mature Nf Xyn11A and recombinant Xyn11A polypeptides, named as r33.4 kDa, r23.8 kDa and r22.0 kDa.

SEQ ID NO:24 A nucleotide sequence for the NruI recognition site introduced into a Kex2 linker SEQ ID NO:25 A nucleotide sequence for the Kex2 linker which facilitates the construction of fusions List of Nucleotide Sequence Accession Numbers AJ508952 xyn11A nucleotide sequence of *N.flexuosa* DSM43186

AJ508953 xyn10A nucleotide sequence of *N.flexuosa* DSM43186

Donor Organisms

*Nonomuraea flexuosa* DSM43186 (ATCC35864)

General Description of the Invention

| Abbreviations and Nomenclature | |
|---|---|
| Nf | *Nonomuraea flexuosa* |
| xyn10A | gene for family 10 xylanase |
| Xyn10A | protein for family 10 xylanase |
| xyn11A | gene for family 11 xylanase |
| Xyn11A | protein for family 11 xylanase |
| CBM, CBD | carbohydrate binding module/domain, Partial structure of carbohydrate degrading enzyme |
| CBM | carbohydrate binding module herein the term CBM is used for truncated carbohydrate degrading enzymes |
| CBD | carbohydrate binding domain herein the term CBD is used for domains of carrier protein |
| cel7A (cbh1) | cellobiohydrolase 1 gene in *Trichoderma reesei* |
| cel7B (egl1) | endoglucanase 1 gene of *Trichoderma reesei* |
| cel6A (cbh2) | cellobiohydrolase 2 gene of *Trichoderma reesei* |
| cel5A (egl2) | endoglucanase 2 gene of *Trichoderma reesei* |
| man5A | mannanase gene of *Trichoderma reesei* |
| Nf xyn11A | *N.flexuosa* xylanase gene from the family 11 |
| Nf xyn10A | *N.flexuosa* xylanase gene from the family 10 |
| am35 | Nf xyn11A gene encoding the full-length form of the Nf Xyn11A mature protein (amino acids $D_{44}$-$N_{344}$) |
| am24 | shortened form of Nf xyn11A encoding the truncated form of the Nf Xyn11A mature protein (amino acids $D_{44}$-$L_{263}$) |
| am35* | am35 but including the following changes in codons: $Gly_{53}$ GGG to GGC, $Ala_{66}$ GCG to GCC, $Gly_{68}$ GGG to GGC, $Arg_{85}$ CGG to CGC, $Gly_{88}$ GGG to GGC, $Gly_{100}$ GGA to GGC, $Arg_{101}$ CGG to CGC, $Arg_{102}$ CGG to CGC and $Val_{104}$ GTG to GTC |
| am24* | am24 but including the same changes in codons as am35* |
| am50 | Nf xyn10A gene encoding the full-length form of the Nf Xyn10A mature protein (amino acids $A_{45}$-$A4_{492}$) |
| AM35 | same as r33.4 kDa, see below, encoded by am35 and am35* |
| AM24 | truncated form from AM35, encoded by am24 and am24* (amino acids $D_{44}$-$L_{263}$) |
| r33.4 kDa | full-length recombinant Nf Xyn11A mature protein (amino acids $D_{44}$-$N_{344}$) |
| r23.8 kDa | cleavage form of the full-length recombinant Nf Xyn11A mature protein (amino acids $D_{44}$-$V_{260}$) |
| r22.0 kDa | cleavage form of the full-length recombinant Nf Xyn11A mature protein (amino acids $D_{44}$-$N_{236}$) |
| AM50 | full-length recombinant Nf Xyn10A mature protein (amino acids $A_{45}$-$A_{492}$), encoded by am50. |

Classification of Carbohydrate-Active Enzymes

Information about the nomenclature of carbohydrated degrading enzymes including cellulases, xylanases, mannanases, and others can be found at Coutinho, P. M. &

Henrissat, B. (1999) Carbohydrate-Active Enzymes server at URL: http://afmb.cnrs-mrs.fr/CAZY/.

Terminology

In the present invention most definitions have the same meaning they generally have in the corresponding scientific fields. Some terms are used in somewhat different way. Therefore, they are explained in more detail below.

The term "carbohydrate degrading (CD) enzyme" means an enzyme active on carbohydrate substrate and having a catalytic module (CAT) and a carbohydrate binding module (CBM) separated by a linker region. The terms "domain" or "region" are also used for the term "module". Bacterial carbohydrate degrading enzymes are obtainable from several different bacterial strains, including actinomycete strains of *Nonomuraea, Thermomonospora*, particularly *Nonomuraea flexuosa* or *Thermomonospora fusca*. The method seems to be applicable to enzymes obtainable from some other microorganisms, for example, xylanases obtainable from *Chaetomium,* particularly *C. thermophilum*, which is a filamentous fungus. Carbohydrate degrading enzymes include cellulose and hemicellulose degrading enzymes, particularly some specific mannan degrading enzymes. Particularly useful are thermostable xylanases including Nf Xyn10A or Nf Xyn11A. Information about carbohydrate degrading enzymes and their structures are found for example in Gilkes, et al., Eur. J. Biochem., 202, 367-377. 1991, Teeri, et al., J. Biotechnol., 24, 169-176, 1992, Stålbrand, et al., Appl. Environ. Microbiol., 61, 1090-1097, 1995, Tomme, et al., (1995) Enzymatic Degradation of Insoluble Polysacharides (Saddler & Penner, Eds.) Cellulose-binding domains: classification and properties. pp 142-163, American Chemical Society, Washington). In most carbohydrate degrading enzymes the CBM is situated in the C-terminal end of the molecule, but some enzymes, for example *T. reesei* Cel6 (CBHII) and Cel5A (EGII) have their CBM in the N-terminal end of the enzyme. The invention, it is the provision of higher production levels by removal of the CBM or part of it or the CBM and the linker or part of it of the bacterial carbohydrate degrading enzyme is believed to work even if the CBM is not situated in the C-terminal end of carbohydrate degrading enzyme used to exemplify the invention.

The term "truncated form of the carbohydrate degrading enzyme" means an enzyme, particularly a bacterial enzyme, for example, from an actinomycetes strain which lacks part of the amino acid sequence. Typically, this means that a part or all of the CBM, or alternatively all of the CBM and a part or all linker region is missing from the truncated form. Truncated form of the enzyme contains an intact catalytic domain or at least a region of the catalytic domain which is essential in catalytic activity of the carbohydrate degrading enzyme (CD). The truncated enzyme is expressed and secreted under the control of suitable regulatory sequences, including promoters and signal sequences.

The term "catalytically active region of CAT" means that the region carries at least the enzyme active site, which provides the specificity for its particular substrate and contributes the amino acid residues that directly participate in the making and breaking of chemical bonds. The active site amino acid residues are conserved within different CD families. The active sites of family 10 and family 11 endo-1,4-xylanases, for example, contain two conserved glutamic acids, which are essential for catalytic activity. The catalytically active region of CAT has similar catalytic activity than the corresponding intact CAT or the intact carbohydrate degrading enzyme and can be measured, for example, with enzyme activity assays.

The term "DNA construct" means an expression or transformation construct. The DNA construct comprises at least a shortened DNA sequence, which originates from a bacterium and encodes a shortened form of said bacterial carbohydrate degrading enzyme preferably in combination with appropriate regulatory sequences, which include a promoter, a signal sequence with or without a carrier sequence, and a terminator sequence originating from a filamentous fingus. The DNA construct includes at least the DNA sequences, which are essential for competent expression and secretion of the shortened form of the desired carbohydrate degrading enzyme. The DNA constructs can be provided in two different forms, as an expression cassette or an expression plasmid.

In an expression plasmid the DNA construct may further contain plasmid elements and reporter gene sequences for replication and selection in *E. coli*. An expression cassette favourably consists of the DNA sequences, which are essential for the expression and secretion of the bacterial enzymes in filamentous fungi. The expression cassette does not include plasmid elements and reporter sequences. The selection marker can be included in either the expression plasmid/cassette or it can be separately transformed to the filamentous fungal host by using co-transformation method. In other words, plasmid elements and reporter sequences are removed from the expression plasmids in order to obtain the expression cassettes for transformation. However, both forms may include and preferably include sequences, which enable locus targeted transformation in the filamentous fungal host. The DNA construct may thereby be targeted to a selected locus in the genome of the host.

The term "regulatory sequences" means DNA sequences controlling the expression and secretion of the carbohydrate degrading enzyme having the structure defined above. The regulatory sequences used in the present invention preferably originate from filamentous fungi, such as *Aspergillus* and *Trichoderma*, particularly *Trichoderma reesei.*

The regulatory sequences comprise at least one signal sequence derived from a filamentous fungus, and also at least one promoter from a filamentous fungus, including the strong *Trichoderma* cel7A (cbh1) promoter. In a preferred embodiment of the invention the shortened DNA sequence encoding the truncated form of the carbohydrate degrading enzyme, is fused in frame with a DNA sequence encoding a carrier protein (polypeptide). The carrier protein is preferably encoded by DNA sequences, which may be obtained from and put together of domains derived from the same or different filamentous fungi and encode one or more, preferably intact domains of a filamentous fungal secretable enzyme. The structure of an intact domain resembles the corresponding region in the full length enzyme due to correct folding of the primary amino acid sequence. Therefore, secretion pathways of carrier polypeptides containing one or more intact domains of the filamentous fungal secretable enzyme are expected to be similar to the native full length enzyme. Applicable, secretable enzymes may comprise a core domain containing the active or catalytic site of the enzyme and a substrate binding domain or carbohydrate binding domain (CBD) linked by a hinge region, but the carrier protein may also be a secretable enzyme naturally consisting solely of the core region, as exemplified by certain filamentous fungal xylanases, e.g. *T. reesei* XYNI and XYNII. An intact CBD or CBD and linker may also be used in order to achieve a high production level. Different domains or regions of filamentous secretable enzymes derived from different filamentous fungi may be put together in varying and arbitrary order. The DNA sequences encoding the regulatory sequences including the carrier protein may be constructed by combining DNA sequences derived from different filamentous fungal sources.

The most preferred combinations include constructs, wherein the carrier protein is a *T. reesei* Man5A core or Man5A core/hinge region, or a *T. reesei* Cel6A CBD (A, A+B or A+B+B'), wherein A means the substrate binding domain or tail; B means the linker (hinge) region; and B' means a duplicated linker(hinge) region. Said DNA sequences encoding the carrier polypeptide are preferably combined with a cel7A (cbh1) promoter. It is possible to construct a multitude of other combinations. The invention includes but is not limited to the following domains: *Trichoderma* CBDs from Cel6A (CBHII), and Cel5A (EGII) carrying a CBD domain in their N-terminal end, xylanase *Trichoderma* (XYNI, XYNII) and *Trichoderma* CBDs from Cel7A (CBHI), Cel7B (EGI) Cel61A (EGIV), Cel45 (EGV) and Cel74 (EGVI) carrying a CBD in their C-terminal end. *Aspergillus* proteins/polypeptides encoded by glaA (glucoamylase) and *Penicillium* proteins/polypeptides encoded by xynA (Alcocer, et al., Appl. Microbiol. Biotechnol., 60, 726-732, 2003) and the corresponding structures from other organisms.

Some other filamentous fingus secretable proteins having applicable domains are found among the carrier polypeptides described in Gouka, et al., Appl. Microbiol. Biotechnol., 47, 1-11, 1997.

The most preferred combinations include the Man5A core or core/hinge region as a carrier polypeptide, the Kex-2 linker (SEQ ID NO: 21) with or without the additional sequence (SEQ ID NO: 22) preceeding the Kex-2 linker and the truncated forms of AM35 polypeptide, i.e. AM24 (SEQ ID NO: 12), r23.8 kDa polypeptide (SEQ ID NO: 13) or r22.0 kDa polypeptide (SEQ ID NO: 14) or the Man5A core or core/hinge region as carrier polypeptide, the Kex-2 linker (SEQ ID NO: 21) with or without the additional sequence (SEQ ID NO: 22) preceeding the Kex-2 linker and the truncated forms of AM50 polypeptide (SEQ ID NO: 17; SEQ ID NO: 18; SEQ ID NO: 19; SEQ ID NO: 20).

The most preferred combinations further include the Cel6A CBD (A, A+B or A+B+B') region as a carrier polypeptide, the Kex-2 linker (SEQ ID NO: 21) with or without the additional sequence (SEQ ID NO:22) preceeding the Kex-2 linker and the truncated forms of AM35 polypeptide, i.e. AM24 (SEQ ID NO: 12), r23.8 kDa polypeptide (SEQ ID NO: 13) and r22.0 kDa polypeptide (SEQ ID NO: 14) or the Cel6A CBD (A, A+B or A+B+B') region as a carrier polypeptide, the Kex-2 linker (SEQ ID NO: 21) with or without the additional sequence (SEQ ID NO: 22) preceeding the Kex-2 linker and the truncated forms of AM50 polypeptide (SEQ ID NO: 17; SEQ ID NO: 18; SEQ ID NO: 19; SEQ ID NO: 20).

In the present invention the term "filamentous fungus" is used in several connections including host organism and donor organism for regulatory sequences. The preferred filamentous fungi, include any transformable filamentous fungi in which expression can be achieved, most preferably they include but are not limited to *Trichoderma, Aspergillus*, and *Penicillium* strains. Particularly preferred hosts and donor organisms are *Trichoderma reesei, Trichoderma longibrachiatum, Trichoderma viridae, Trichoderma koningii, Aspergillus niger, Aspergillus* sp., *Penicillium* sp., *Humicola* sp., including *Humicola insolens, Chrysosporium* sp., *Fusarium* sp., *Hypocrea* sp. and *Emericella* sp., etc.

The term "an increased production level" means that the production level of the truncated form of the bacterial carbohydrate degrading enzyme is higher than the production level of the full length enzyme in a similar construct which is otherwise identical but differs in the length of the DNA sequence encoding the bacterial enzyme. The increase in production level is in this case measured as an increase of activity (Table 4), because the increase in activity in this case is independent of the specific activity, as demonstrated by the results shown in Table 1. It is to be noted that the increase in efficacy or in the production level is measured as xylanase activity from the culture media of isogenic single-copy transformants or host cells containing only one copy of the DNA construct in question. Furthermore, the isogenic single copy is located in the same locus, for example in the cbh1 locus. Therefore, it is unambiguously excluded that the increase in production level would be caused by introduction of multiple copies of the DNA construct or of differences in the site of integration. The transformants analysed differ only in that the DNA constructs of the present invention comprise a shortened DNA sequence encoding a truncated form of the full length carbohydrate degrading enzyme, whereas the prior art DNA construct comprises a DNA sequence encoding the corresponding full length enzyme. The production levels are accordingly based upon unambigous comparisons.

BRIEF DESCRIPTION OF THE DRAWINGS/FIGURES

Figure 1:
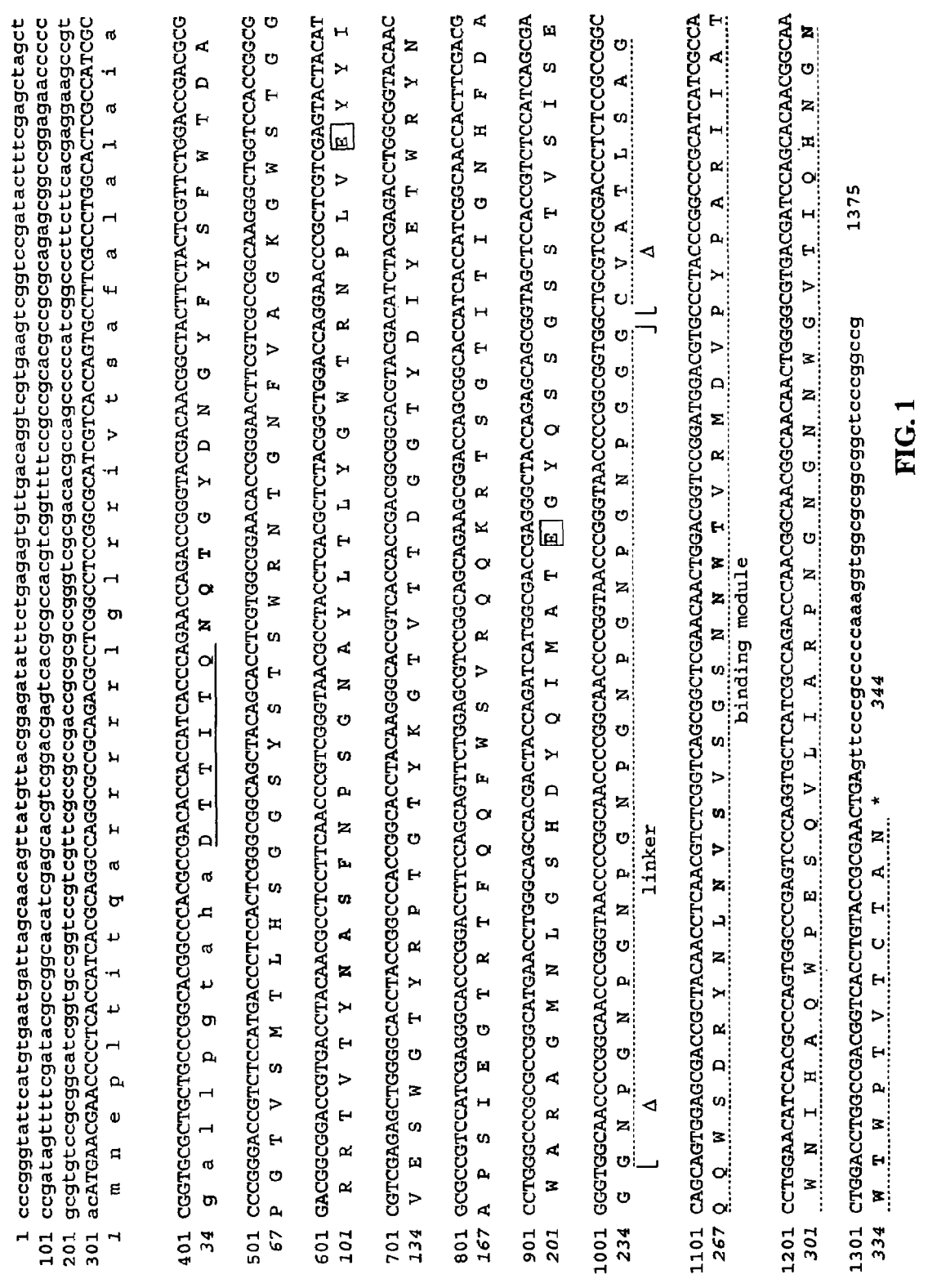

FIG. 1 shows the nucleotide sequence of the *Nonomuraea flexuosa* xyn11A gene and the deduced amino acid sequence. The stop codon is shown by an asterisk below the sequence. The mature N-terminal amino acid sequence, determined from the purified Xyn11A protein, is underlined. The active site glutamic acids are marked with an open box. The location of the linker and carbohydrate-binding module is indicated by a dotted line below the amino acid sequence. The cleavage sites of the r23.8 kDa and r22.0 kDa polypeptides are marked by a triangle. The sites for putative N-glycosylation in eukaryotic hosts are bolded.

FIG. 2A shows the nucleotide sequence of the *N. flexuosa* xyn10A gene and the deduced amino acid sequence. The stop codon is shown by an asterisk below the sequence. The tryptic peptide sequences, obtained from the purified Xyn10A protein, are shown by underlining below the amino acid sequence. The active site glutamic acids are marked with an open box. The putative location of the linker and carbohydrate-binding module, consisting of the $\alpha$, $\beta$ and $\gamma$ subdomains (Fujimoto, et al., J. Mol. Biol., 300:575-585, 2000) is indicated by a dotted line below the amino acid sequence. The QxW repeats present in the "ricin superfamily" CBMs (Fujimoto, et al., J. Mol. Biol., 300, 575-585, 2000; Hirabayashi, et al., J. Biol. Chem., 273, 14450-14460, 1998) are bolded. The nucleotide sequence continues in FIG. 2B.

FIG. 2B shows the continuation of the nucleotide sequence depicted in FIG. 2A.

FIG. 3 shows the structure of the expression cassette pALK945, constructed to produce the recombinant mature *N. flexuosa* Xyn11A protein using *T. reesei* Man5A core/hinge as a carrier polypeptide. The gene fusion was expressed from cel7A promoter and termination of transcription was ensured by using cel7A terminator sequence. The man5A sequence included encoded the amino acids $M_1$-$G_{406}$ (Stålbrand, et al., J. Biotechnol., 29, 229-242, 1993). The amdS gene (Kelly and Hynes, EMBO J., 4: 475-479) was included as a transformation marker and the cel7A 3'-flanking region was included, together with the cel7A promoter, to target the expression cassette into the cel7A locus by homologous recombination. Synthetic linker sequence coding for an additional Arg was included to ensure cleavage of the fusion protein. The amino acids coded by the man5A sequence are in regular font, those of xyn11A in italics and the synthetic amino acid for proteolytic cleavage is in bold.

Figure 4:
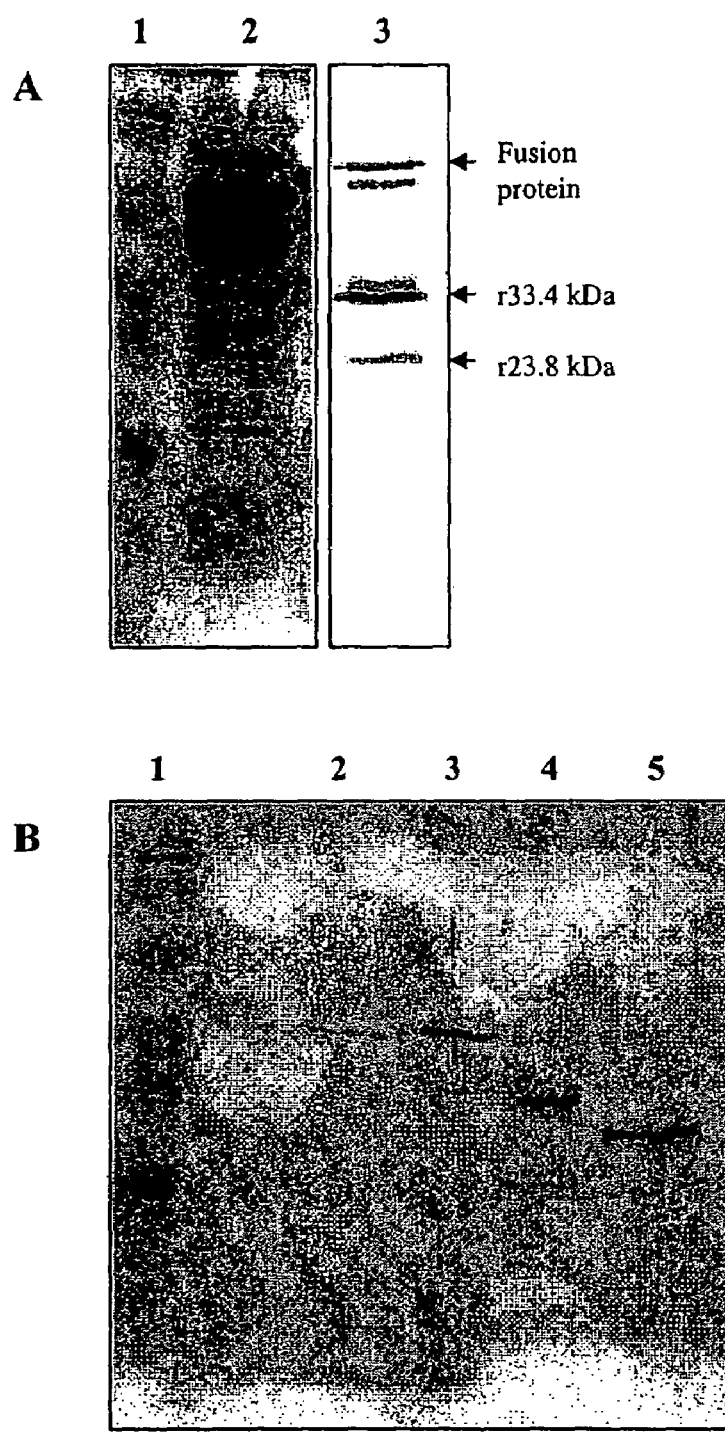

FIG. 4A shows a sample of T. reesei cultivation medium from which the recombinant xylanase polypeptides (Example 7) were purified run on SDS-polyacrylamide gel after Coomassie Blue staining (lane 2) and after Western blot analysis (lane 3). The location of the r33.4 kDa and r23.8 kDa polypeptides and the fusion protein are shown by arrows. The r22.0 kDa form was not visible in the gel/Western blot shown, due to its low amount in the culture supernatant. Sizes of the molecular weight markers (on lane 1) were, from the top to the bottom: 104, 80, 46.9, 33.5, 28.3, 19.8 kDa. A polyclonal antibody made against the purified Nf Xyn11A was used for detection of the heterologous xylanase forms from the Western blot filter.

FIG. 4B shows the samples of purified native Nf Xyn11A (lane 2), and the recombinant xylanase forms r33.4 kDa polypeptide (lane 3), r23.8 kDa polypeptide (lane 4) and r22.0 kDa polypeptide (lane 5) run on SDS-polyacrylamide gel and stained with Coomasie Blue. The molecular weight markers (lane 1) are the same as in FIG. 4A.

FIG. 5A shows temperature profiles of the purified Xyn11A xylanases at pH 5. Effect of temperature was determined by incubation of the reaction mixture at pH 5 and different temperatures for 60 min. The relative (%) activity is expressed as percentage of maximum activity at the optimum temperature. The relative activities at pH 6 (not shown) were similar to those obtained at pH 5.

FIG. 5B shows temperature profiles of the purified Xyn11A xylanases at pH 7. Effect of temperature was determined by incubation of the reaction mixture at pH 7 and different temperatures for 60 min. The relative (%) activity is expressed as percentage of maximum activity at the optimum temperature.

FIG. 5C shows temperature profiles of the purified Xyn11A xylanases at pH 8. Effect of temperature was determined by incubation of the reaction mixture at pH 8 and different temperatures for 60 min. The relative (%) activity is expressed as percentage of maximum activity at the optimum temperature.

FIG. 6A shows residual activity of the purified enzymes after incubation at 80° C. at pH 5. Thermostability was determined by incubating the Xyn11A polypeptides at pH 5 for a period of 0, 15, 30, 45, 60, 75, 90, 150 and 245 min in the absence of substrate, after which the residual activities were measured at pH 7 and 70° C. for 5 min.

FIG. 6B shows residual activity of the purified enzymes after incubation at 80° C. at pH 7. Thermostability was determined by incubating the Xyn11A polypeptides at pH 7 for a period of 0, 15, 30, 45, 60, 75, 90, 150 and 245 min in the absence of substrate, after which the residual activities were measured at pH 7 and 70° C. for 5 min.

Figure 7:
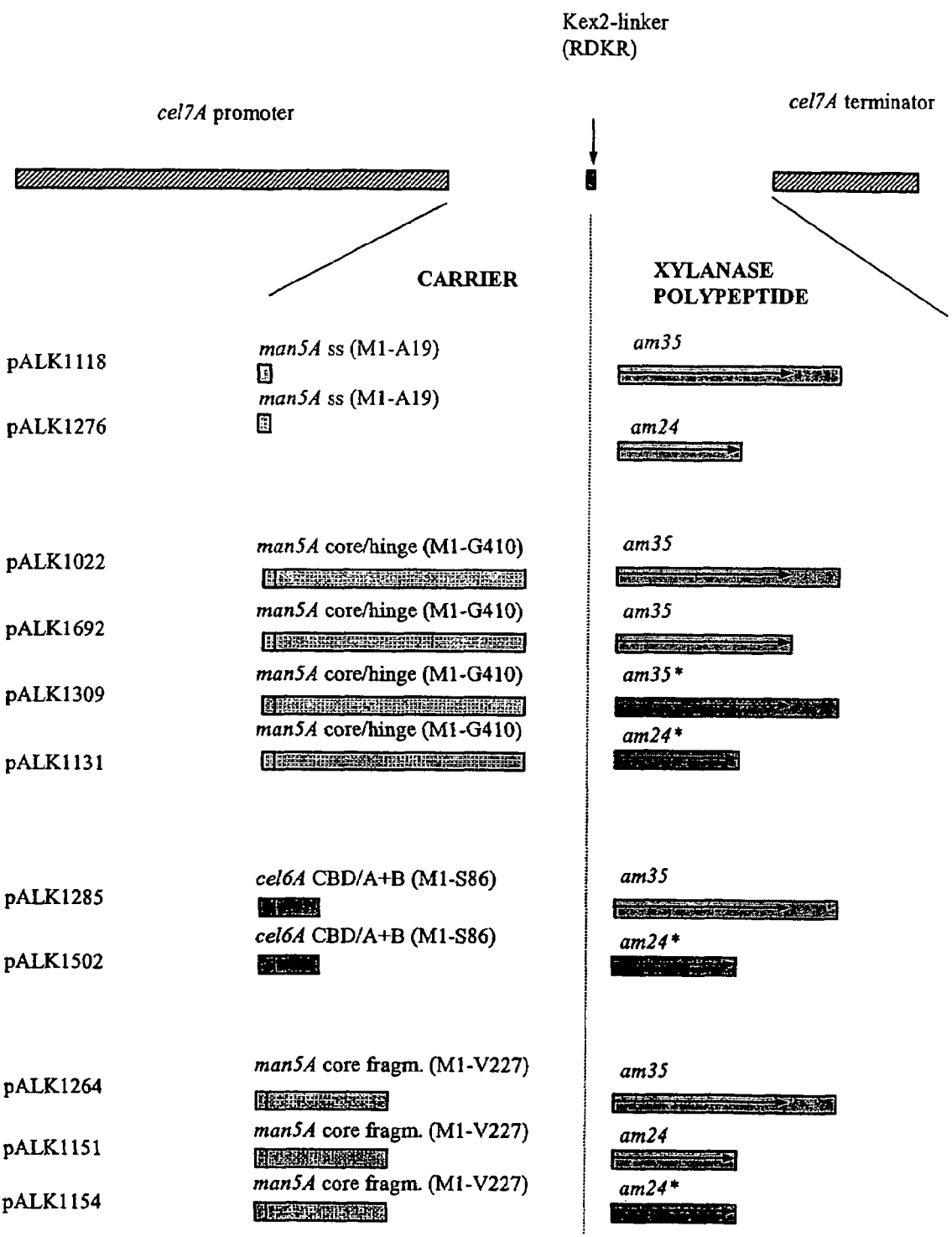

FIG. 7 shows the overall structure of the expression cassettes constructed to study the effect of the truncation of the am35 gene on xylanase production levels in Trichoderma reesei. The gene fusions were expressed from cel7A promoter and termination of transcription was ensured by using cel7A terminator sequence. The carrier polypeptides used were encoded either by the man5A core/hinge sequence ($M_1$-G410 in pALK1022, pALK1692, pALK1309 and pALK1131), the cel6A CBD sequence ($M_1$-$S_{86}$) in pALK1285 and pALK1502 or the man5A sequence encoding for a fragment of the Man5A core ($M_1$-$V_{227}$ in pALK1264, pALK1151 and pALK1154). The Cel6A CBD block A codes for the tail of the protein and B for the hinge region. In the plasmids pALK1118 and pALK1276 the xylanase gene was fused to the man5A signal sequence. A synthetic linker sequence coding for a Kex2-like protease cleavage signal Lys-Arg (included as RDKR (SEQ ID NO:18)) was included in all the constructs to ensure cleavage of the fusion protein. The expression cassette pALK1264, pALK1131 and pALK1134 also included an additional sequence coding for GQCGG (SEQ ID NO:19) preceding the Kex2 site. The amino acids coded by am35 (SEQ ID NO: 2) and am35* (SEQ ID NO: 4) are $D_{44}$-$N_{344}$ (the full length mature protein, FIG. 1; SEQ ID NO: 11) and by the truncated am35/am35* sequences (am24 (SEQ ID NO: 3) and am24*; SEQ ID NO: 5) are $D_{44}$-$L_{263}$ (FIG. 1; SEQ ID NO: 12). In am35* (SEQ ID NO: 4) and am24* (SEQ ID NO: 5) nine codons have been changed as described in Example 10. The changes do not alter the encoded amino acid sequences. The amdS marker gene and the cel7A 3'-flanking region (to target the expression cassette into the cel7A locus by homologous recombination) were included in all the constructs after the cel7A terminator sequence (identically to the pALK945 expression cassette shown in FIG. 3).

Figure 8:
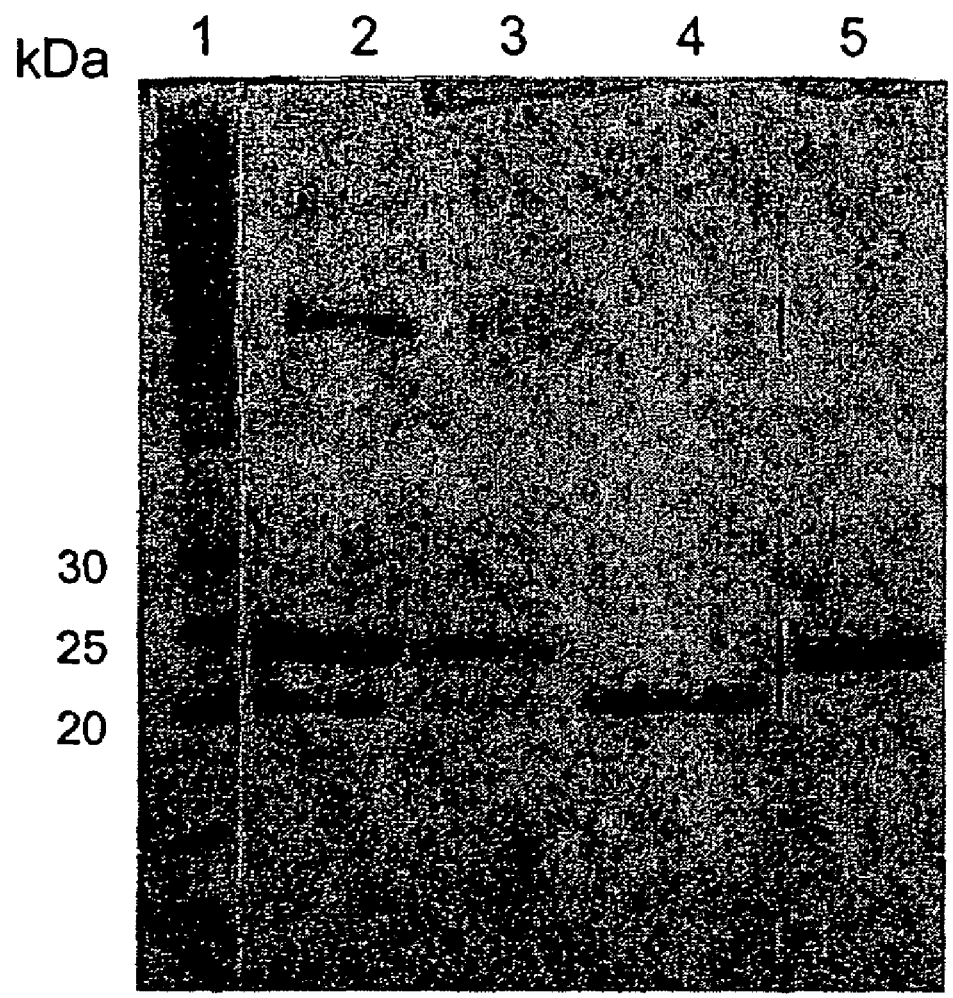

FIG. 8 shows a Coomassie Blue stained SDS-polyacrylamide gel, in which a sample of the culture supernatant of a T. reesei transformant producing the truncated form of Nf Xyn11A xylanase (AM24) was run. The Cel6A CBD was used as a carrier polypeptide. The purified r23.8 and r22.0 kDa forms were run in parallel on the gel. Lanes: 1. A molecular weight marker (the molecular mass of the relevant marker proteins is shown), 2. and 3. Culture supernatant from a T. reesei transformant producing the truncated Xyn11A, 3. Purified r22.0 kDa xylanase, 5. Purified r23.8 kDa xylanase.

Figure 9A:
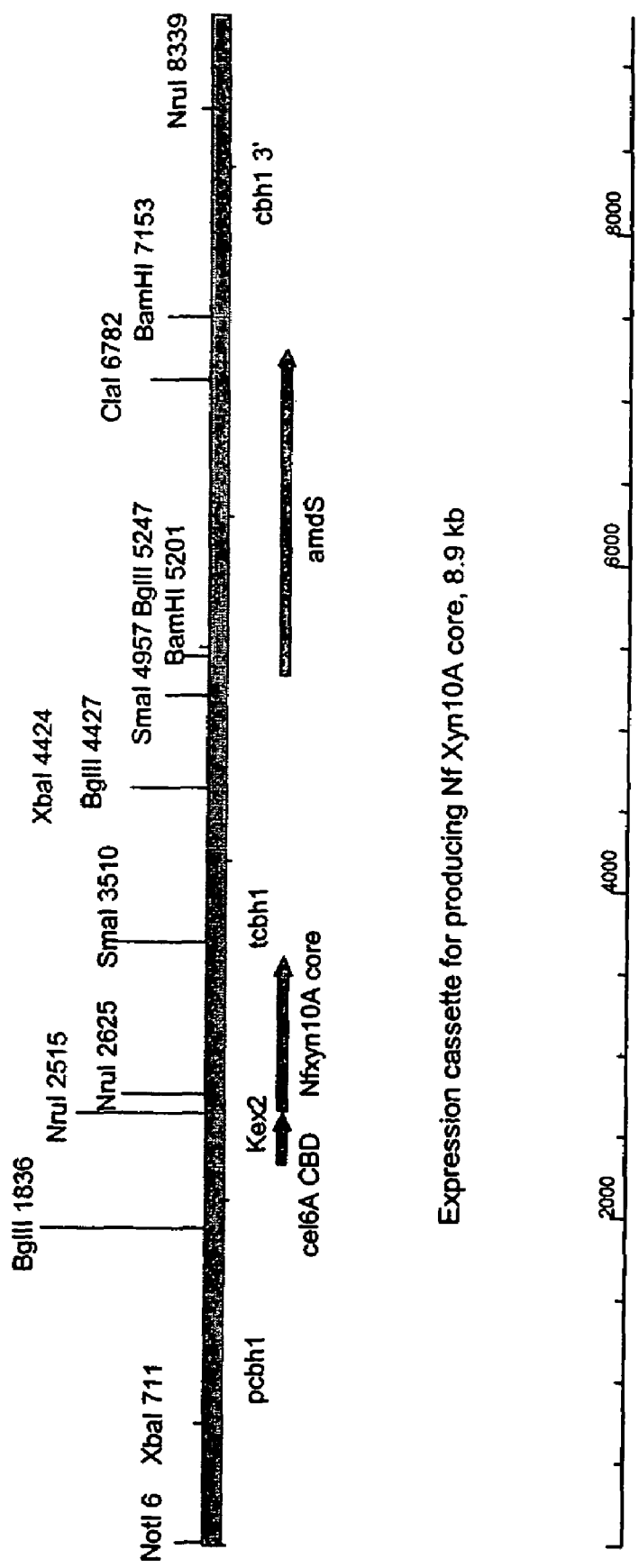

FIG. 9A shows the expression cassette for producing a truncated form of Nf Xyn10A, the Nf Xyn10A core, in T. reesei. The core includes the amino acids $A_{45}$-$N_{345}$ (FIG. 2; SEQ ID NO: 18). The cel7A promoter, cel6A signal peptide and cel7A terminator sequences are used (as in the construct pALK1285 and pALK1502, FIG. 7) for Nf Xyn10A production. The Cel6 CBD (A+B) is used as a carrier polypeptide (as in the constructs pALK1285 and pALK1502, FIG. 7). A sequence encoding a Kex2 site (RDKR (SEQ ID NO:18)) is included between the carrier and the xylanase sequences. The amdS marker and the cbh1 3'-fragment are included as in the constructs for producing Nf Xyn11A.

Figure 9B:
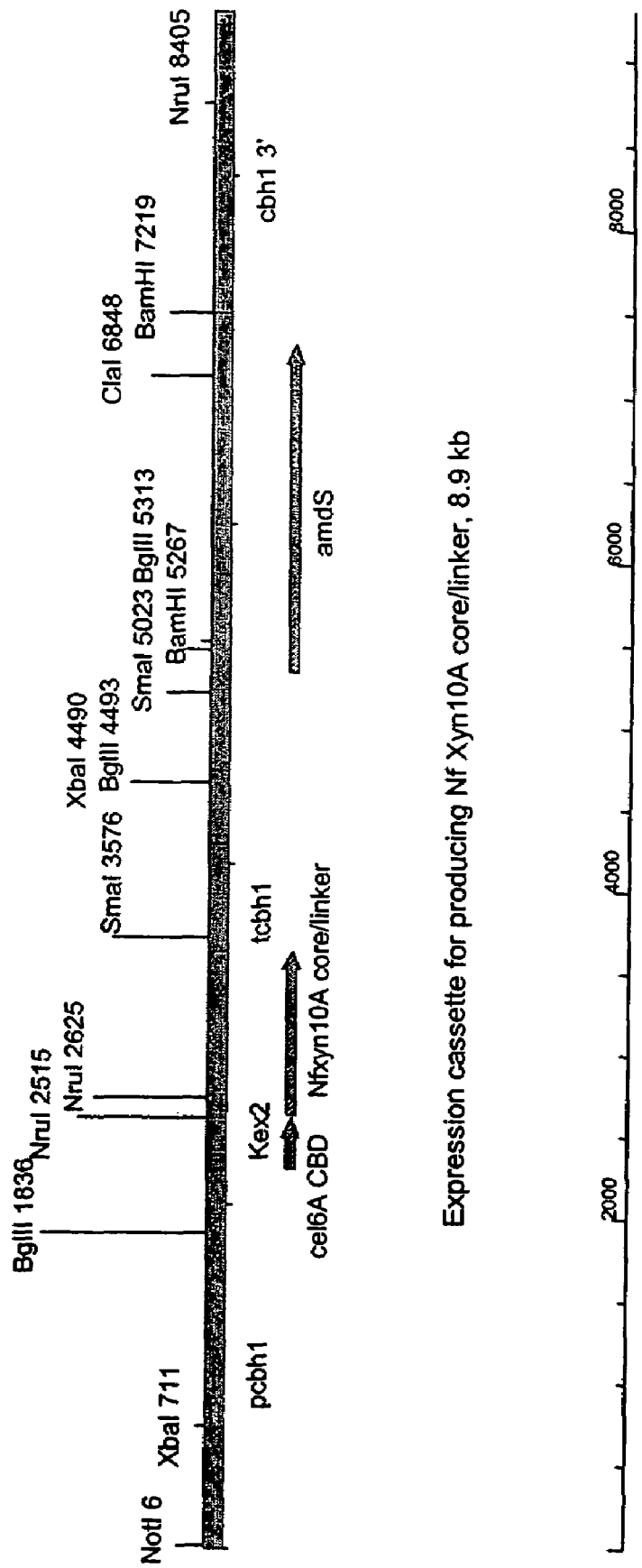

FIG. 9B shows the expression cassette for producing a truncated form of Nf Xyn10A, the Nf Xyn10A core/linker in T. reesei. The core/linker includes the amino acids $A_{45}$-$S_{367}$ (FIG. 2; SEQ ID NO: 17). The other sequences (cel7A promoter, cel6A signal peptide, cel6A CBD encoding sequence, cel7A terminator, the sequence encoding the Kex2 site, the amdS marker and the cbh1 3'-fragment) are as in the constructs in FIG. 9A.

Figure 9C:
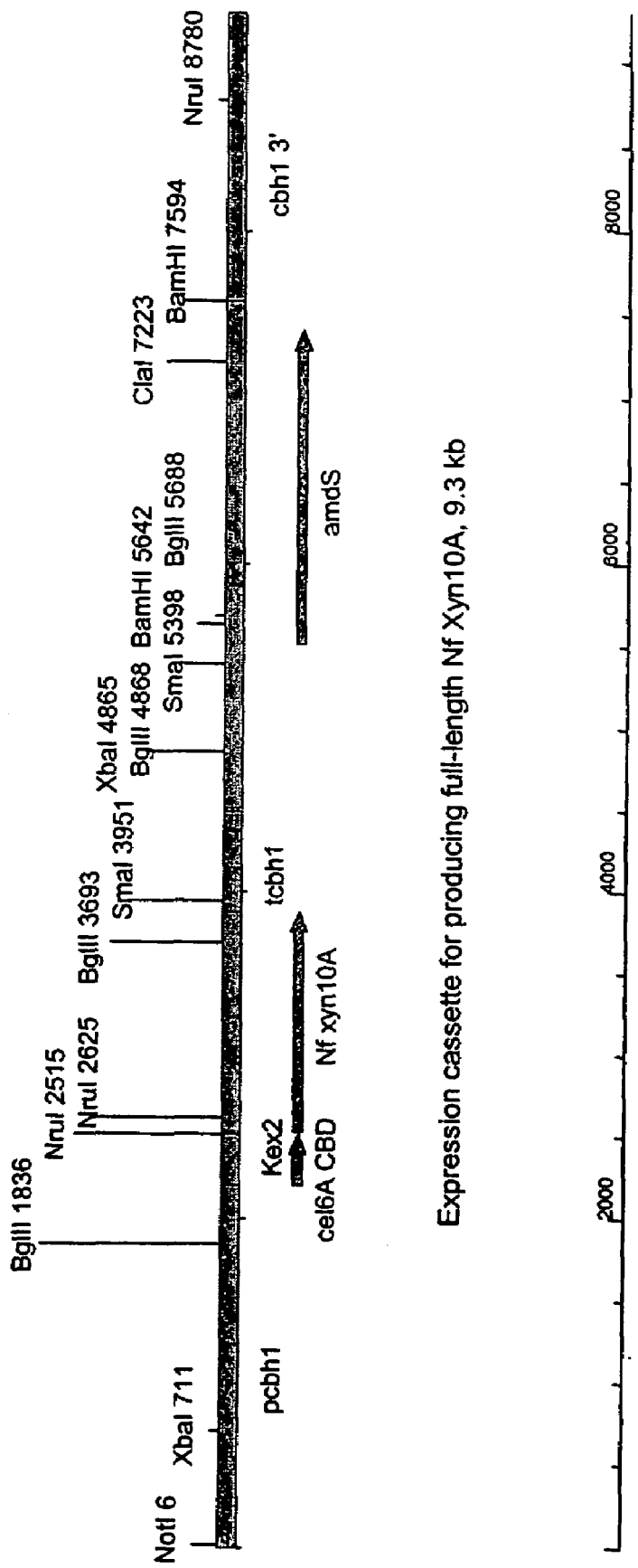

FIG. 9C shows the expression cassette for producing the full-length Nf Xyn10A in T. reesei. The full-length xylanase includes the Nf Xyn10A amino acids $A_{45}$-$A_{492}$ (the full-length protein from the N-terminal end, FIG. 2; SEQ ID NO: 16). The other sequences (cel7A promoter, cel6A signal peptide, cel6A CBD encoding sequence, cel7A terminator, the sequence encoding the Kex2 site, the amdS marker and the cbh1 3'-fragment) are as in the constructs in FIG. 9A.

DETAILED DESCRIPTION OF THE INVENTION

In the present invention it is demonstrated that production levels of carbohydrate degrading (CD) enzymes, particularly bacterial enzymes, produced in a Trichoderma reesei host may be increased not only by fusion strategies as described by Paloheimo, et al., Appl. Environ. Microb., 69, 7073-7082, 2003, but also by using truncated DNA sequences originating from actinomycetes strains including *Nonomuraea flexuosa*. By expressing said shortened DNA sequences yields of the desired truncated carbohydrate degrading enzyme increase. The functions, including specific activities of the truncated enzymes are the same or similar to those obtained with the corresponding full-length enzyme. The preparations obtained with the method and constructs of the present invention are useful in industrial processes requiring high temperatures and pHs.

In the following examples the invention is described in more detail.

EXAMPLES

Example 1

Methods Used in the Analysis and Characterisation of Proteins (Polypeptides) Protein and Enzyme Assays Protein concentrations in the culture media and purified enzyme samples were assayed after TCA precipitation by the method of Lowry, et al. (J. Biol. Chem., 193, 265-275, 1951) using bovine serum albumin as a standard protein. During enzyme purifications, proteins were monitored at 280 nm. Xylanase activity was assayed by using 1% (w/v) birch xylan (Roth no. 7500, Roth, Karlsruhe, Germany) as a substrate in 50 mM McIlvaine citrate-phosphate buffer according to the method of Bailey et al., (J. Biotechnol., 23, 257-270, 1992). During enzyme purification and determination of the specific activity of the pure proteins the assay was performed at pH 7, 60° C. for 5 min, otherwise as stated in the figure legends. For characterization of the purified Xyn11A polypeptides the buffer was supplemented with 0.1% BSA, except for the determination of thermostability which was performed without BSA.

Protein Electrophoresis

The samples were run on 12% polyacrylamide slab gels containing 0.1% SDS on a Mini Protean II electrophoresis system (Bio-Rad Laboratories, Inc., Hercules, Calif.) and stained with Coomassie Brilliant Blue R250. Detection of the xylanase and xylanase polypeptides on the Western blot filters was carried out with a polyclonal rabbit antibody raised against the purified Nf Xyn11A xylanase prepared at Diabor Ltd. (Oulu, Finland) and the Protoblot AP System (Promega Corp., Madison, Wis.).

Preparation and Sequencing of Peptides

Purified fractions containing xylanase activity were subjected to tryptic digestion as described in Fagerström and Kalkkinen (Biotechnol. Appl. Biochem., 21, 223-231, 1995). Sequencing was performed by Edman degradation in a gas-pulsed-liquid-phase sequencer (Kaikkinen and Tilgmann, J. Protein Chem. 7:242-243, 1988) and the phenylthiohydantoin amino acids were analyzed on-line by using narrow bore reverse phase HPLC. For N-terminal sequencing, SDS-PAGE gels were blotted on a PVDF filter and the protein spots were directly subjected to Edman degradation as above. The sequencing was performed at the Institute of Biotechnology (Helsinki, Finland). The C-termini of the purified recombinant polypeptides were determined at the Protein Analysis Center at the Karolinska Institutet (Stockholm, Sweden).

Estimation of pI and Determination of the Molecular Mass

The pI of the purified xylanases was estimated by chromatofocusing on a 4 ml prepacked Mono P HR 5/20 column (Amersham Biosciences) equilibrated with 75 mM Tris-$CH_3COOH$ (pH 9.5) and eluted with 10% Polybuffer 96 (Amersham Biosciences) in 75 mM Tris-$CH_3COOH$ (pH 6.3). The pH was measured from the fraction containing xylanase activity. Molecular masses of the purified xylanases were determined by Bruker Biflex Reflector MALDI-TOF mass spectrometer (Bruker Daltonik GmbH, Bremen, Germany).

Example 2

DNA Techniques Used in Constructing Plasmids and Strains

Standard DNA methods (Sambrook, et al., Molecular cloning: a laboratory manual, $2^{nd}$ ed. Cold Spring Harbor Laboratory, Cold Spring Harbor, 1989) were used in constructing plasmids, transforming *E. coli* and performing Southern blots. Each enzyme and kit was used according to the instructions from the supplier. The enzymes for DNA modifications were purchased from Roche Diagnostics GmbH (Mannheim, Germany), New England Biolabs (Beverly, Mass.) and Finnzymes (Espoo, Finland). Qiagen columns (Qiagen GmbH, Hilden, Germany) or Magic Miniprep kits (Promega, Madison, Wis.) were used in the plasmid isolations. The oligonucleotides were either synthesized using ABI 381A DNA synthesizer or ordered from Sigma-Genosys. The sequencing reactions were analysed either by using ABI 373A or ABI Prism™ 310 Genetic Analyzer (Applied Biosystems, Foster City, Calif.). Polymerase chain reactions (PCR) were performed using PTC-100 Programmable Thermal Controller (MJ Research Inc, Watertown, Mass.). DNA fragments for subdloning and transformations were isolated from low melting point agarose gels (Bio-Whittaker Molecular Applications Inc., Rockland, Me.) by the freeze-thaw-phenol method (Benson, BioTechniques, 2, 66-68, 1984), by using β-agarase (New England Biolabs) or by using the Qiaex II Gel Extraction Kit (Qiagen GmbH).

The genomic DNAs were isolated as described in (Raeder and Broda, Lett. Appl. Microbiol., 1, 17-20, 1985). Digoxigenin labeled (Roche Diagnostics GmbH) expression cassettes were used as probes in the Southern blot hybridizations.

Example 3

Microbial Strains Used as Hosts and in Constructing Plasmids, Growth Media and Growth Conditions Plasmids were propagated in *Escherichia coli* XL1-Blue or XL10-Gold (Stratagene, La Jolla, Calif.). The vector backbones used in the plasmid constructions were pUC18 (EMBL Database Accession No L09136), pUC19 (L09137), pBluescript SK– and pBluescript II KS+ or KS– (Stratagene). All *E. coli* cultivations were performed over night at 37° C. in Luria-Bertani medium into which ampicillin had been added (50 μg/ml).

The *Trichoderma reesei* strains ALKO3620 and ALKO4468 were used as parents for the transformations. *T. reesei* ALKO3620 is an endoglucanase II-negative strain. It was constructed from the low protease mutant strain ALKO2221, derived from the strain VTT-D-79125 (3) by UV-mutagenesis (Bailey and Nevalainen, Enzyme Microb. Technol., 3, 153-157, 1981) as follows. The endoglucanase 2 gene (cel5A or egl2, originally named as egl3; (Saloheimo, et al., Gene 63, 11-21, 1988)) was replaced by the phleomycin resistance-encoding marker gene from *Streptoalloteichus hindustanus*, Sh ble (Drocourt, et al., Nucleic Acids Res., 18, 4009, 1990). The 3.3 kb BglII-XbaI fragment from the plasmid pAN8-1 (Matheucci, et al., Gene, 8, 103-106, 1995), containing the ble gene flanked by the *Aspergillus nidulans* gpd promoter and trpC terminator was used. The cel5A flanking sequences in the replacement cassette (the 5′-region being the 1.4 kb XhoI-SacI fragment about 2.2 kb upstream from the cel5A gene and the 3′-region the 1.6 kb AvrII-SmaI fragment about 0.2 kb from the end of the cel5A gene) were isolated from the egl3 λ clone (Saloheimo, et al., Gene, 63, 11-21, 1988). The strategy for the replacement was as described in (Suominen, et al., Mol. Gen. Genet., 241, 523-530, 1993). *T. reesei* ALKO4468 is an endoglucanase I and II-negative strain. It was constructed from the strain ALKO3620 by further replacing the endoglucanase 1 gene, cel7B (egl1, Penttilä, et al., Gene, 45, 253-263, 1986), by the *E. coli* hygromycin B phosphotransferase gene, hph (Gritz, et al., Gene, 45, 179-188, 1983), conferring resistance to hygromycin B. The 1.7 kb NotI-NsiI fragment from the plasmid pRLM$_{EX}$30 (Mach, et al., Curr. Genet., 25, 567-570, 1994) was used in which of the hph gene is expressed from the *T. reesei* pyruvate kinase (pki) promoter and the transcription is terminated using the cel6A terminator sequences. The plasmid pRLM$_{EX}$30 was kindly provided by Prof. Christian P. Kubicek (Institut für Biochemische Technologie, TU Wien, Austria). The cel7B flanking regions were as described in (Suominen, et al., Mol. Gen. Genet., 241, 523-530, 1993). The single-copy replacements of the cel5A and cel7B genes by the marker genes in *T. reesei* ALKO3620 and ALKO4468 were verified by Southern blot analysis, as described in (Suominen, et al., Mol. Gen. Genet., 241, 523-530, 1993).

*T. reesei* strains were sporulated on PD agar slants (Potato Dextrose Broth, Difco, Detroit, Mich.). The transformants were selected on *Trichoderma* minimal medium containing acetamide as a nitrogen source (Penttilä, et al., Gene, 61, 155-164, 1987). The fungal mycelia for DNA isolations were obtained after growing the strains for two days on *Trichoderma* minimal medium containing 2% proteose peptone (Difco). Complex lactose-based cellulase-inducing media (Joutsjoki, et al., Curr. Genet., 24, 223-228, 1993) were used for enzyme production in shake flasks and fermentations. The transformants were screened using 50 ml cultivations and the mycelium for the RNA isolations was collected from 200 ml cultivations. The shake flask cultivations were grown for 7 days at 30° C., 250 rpm. The laboratory scale fermentor cultivations were performed for 5 days in 1 1 Braun Biostat M fermentors (B. Braun).

Example 4

Cultivation of *Nonomuraea flexuosa* for Enzyme Production

*Nonomuraea flexuosa* DSM43186 (ATCC35864) was cultivated on rolled oats mineral medium plates (medium no. 84, Deutsche Sammlung von Microorganismen und Cellkulturen GmbH Catalogue of Strains, 1983) at 50° C. A sporulating colony was inoculated in XPYB medium, the GPYB medium (Greiner-Mei, et al., Syst. Appl. Microbiol., 9, 97-109, 1987) supplemented with 0.5% oat spelt xylan (Sigma X-0627, Sigma-Aldrich Corp., St. Louis, Mo.) instead of glucose as described in Holtz et al. (Antonie Leeuwenhoek, 59, 1-7, 1991) and was incubated in shake flask for 2 or 3 days (250 rpm, 50-55° C.) after which the shake flask culture was used as a seed culture for the fermentation. The laboratory scale fermentor cultivations were performed for 3 days at 50° C. in 1 liter Braun Biostat M fermentors (B. Braun, Melsungen AG, Melsungen, Germany) in the medium described above.

Example 5

Heterologous Production of the Thermostable *Nonomuraea flexuosa* AM35 Xylanase in *Trichoderma*

The gene coding for the Nf Xyn11A (AM35) xylanase (am35 or Nf xyn11A; EMBL accession no AJ508952) was isolated from a lambda ZAP Express® library prepared from partially digested (Sau3A) and size-fractionated *Actinomadura* (*Nonomuraea*) *flexuosa* DSM43186 (ATCC35864) chromosomal DNA as described in U.S. Pat. No. 6,300,113. The nucleotide sequence of the gene and the deduced amino acid sequence are shown in FIG. 1.

The *T. reesei* transformant strain ALKO4396 producing recombinant Nf Xyn11A was constructed by transforming the expression cassette pALK945 (FIG. 3) to *T. reesei* ALKO3620. The am35 gene is expressed from the cbh1 promoter, as a fusion to a carrier polypeptide encoded by man5A core/hinge sequence. The construction of the plasmid pALK945 and the strain were performed as described in Paloheimo, et al., Appl. Environ. Microbiol., 69, 7073-7082, 2003).

*T. reesei* transformant strain ALKO4396 was sporulated on Potato Dextrose Broth (PD) agar slants (Difco, Detroit, Mich.) at 30° C. For enzyme production in laboratory scale fermentor, the compex lactose based cellulose inducing medium (Joutsjoki et al., Curr. Genet., 24, 223-228, 1993) was used. Fermentations were performed for 5 days in 1 1 Braun Biostat M fermentors.

In addition to the full-length protein, the recombinant *T. reesei* ALKO4396 culture medium was observed, in Western blot, to contain shorter forms of Xyn11A and low amounts of unprocessed Man5A-Xyn11A fusion protein (FIG. 4A).

Example 6

Purification of *N. flexuosa* Xyn11A and the Recombinant Xyn11A Polypeptides

Purification of the native Nf Xyn11A xylanase from the culture media of *N. flexuosa* DSM43186 and the recombinant Xyn11A xylanases from *T. reesei* ALKO4396 was performed by combining ion exchange chromatography, hydrophobic interaction chromatography (HIC) and gel filtration in the following way. The growth medium of 1 1 fermentation was centrifuged at 8,000×g for 30 min at 4° C. The supernatant was adjusted to pH 9.1 with 1 M NaOH and diluted with distilled water (until conductivity 4 mS/cm). This sample was applied to a DEAE Sepharose Fast Flow (Amersham Biosciences AB, Uppsala, Sweden) ion-exchanger (SR column, 5×15.5 cm diameter, 300 ml) equilibrated with 20 mM Na$_2$HPO$_4$ (pH 9.1) using a Fast Protein Liquid Chromatography (FPLC) system (Amersham Biosciences) at 4° C. Flow rate was 20 m/min. Column was washed with 400 ml of 20 mM Na$_2$HPO$_4$ (pH 9.1).

Flow-through proteins were collected into 100 ml fractions. Elution of the bound proteins from the DEAE-column was accomplished by a linear gradient from 20 mM Na$_2$HPO$_4$ (pH 9.1) to 20 mM Na$_2$HPO$_4$ (pH 9.1) containing 0.5 M NaCl at 20 ml/min for 30 min, 5 ml fractions were collected. Finally column was washed with 300 ml of 20 mM Na$_2$HPO$_4$ (pH 9.1) containing 0.5 M NaCl. Fractions were analysed for xylanase activity and purity of proteins was assessed by SDS-PAGE and Western blots.

The flow-through fractions containing xylanase activity were pooled (up to 500-600 ml) and adjusted to contain 2 M NaCl and applied to a Phenyl Sepharose 6 Fast Flow (Amersham Biosciences) column (XR50/30 column, 5×11 cm, 215 ml) equilibrated with 40 mM $Na_2HPO_4$ (pH 9.1) containing 2 M NaCl. After washing with 400 ml of 40 mM $Na_2HPO_4$ (pH 9.1) containing 2 M NaCl elution was performed at 20 ml/min with a two-step gradient. First the proteins were separated using linear gradient (400 ml) of decreasing NaCl concentration (2-0 M) in 40 mM $Na_2HPO_4$ (pH 9.1). After washing with 200 ml of 40 mM $Na_2HPO_4$ (pH 9.1) the proteins were eluted with an increasing gradient (600 ml) of 0-60% ethylene glycol in 40 mM $Na_2HPO_4$ (pH 9.1). Finally the column was washed with 200 ml of 60% ethylene glycol in 40 mM $Na_2HPO_4$ (pH 9.1). 10 ml fractions were collected and analysed for xylanase activity and purity.

Pooled HIC-fractions containing xylanases of different molecular masses were concentrated on an Amicon ultrafiltration unit (Millipore Corp., Billerica, Mass.) with Diaflo® (PM10 62 mm 10 PK) membrane, cut-off 10 kDa. Concentrated sample (10 ml) was subjected to gel exclusion chromatography on a HiLoad 26/60 Superdex 75 prep grade column (2.6×61 cm, 320 ml) equilibrated with 40 mM $Na_2HPO_4$ (pH 9.1) containing 0.1 M NaCl. Elution was performed with 400 ml of 40 mM $Na_2HPO_4$ (pH 9.1) containing 0.1 M NaCl. 6 ml fractions were analysed for xylanase activity purity.

With *N. flexuosa* culture medium roughly half of the xylanase activity loaded on the DEAE Sepharose FF column was found in the flow-through and half was bound to the DEAE column. With *T. reesei* culture medium the xylanase activity was in the flow-through. Most of the native *T. reesei* proteins, e.g. cellulases and the mannanase core/hinge region used as a fusion partner were bound to the DEAE column.

The flow-through fractions containing xylanase activity were pooled for the HIC run. After the Phenyl Sepharose 6 FF column three different forms of the recombinant Xyn11A xylanase were separated (FIG. 4B). The 37 kDa form (on SDS-PAGE, lane 3) corresponds to the native Nf Xyn11A purified from the *N. flexuosa* culture medium. The shorter forms had molecular masses of 30 kDa (lane 4) and 27 kDa (lane 5) on SDS-PAGE. These shorter forms eluted from the Phenyl Sepharose 6 FF column with 0 M NaCl, first the 30 kDa form and the 27 kDa form in subsequent fractions. The 37 kDa polypeptide eluted at 15-30% ethylene glycol concentration. The 30 kDa xylanase was further purified using Superdex 75 gel filtration.

Example 7

Characterization of the Native Xyn11A and the Recombinant Xyn11A Polypeptides

Characteristics of the native Nf Xyn11A and the three recombinant Xyn11A polypeptides are presented in Table 1. The molecular masses estimated from the SDS-PAGE were signicantly higher than deduced from the amino acid sequence or determined by analysing the protein with the mass spectrometer. The molecular mass of the native Nf Xyn11A was determined to be 32857 Da, corresponding the calculated molecular weight (32876 Da) of the mature enzyme. It represents the full-length protein consisting of the catalytic domain and the CBM separated by the linker region. The molecular mass of the recombinant full-length Xyn11A was 33429 Da, which is 572 Da higher than that of the native Nf Xyn11A and 553 Da higher than the calculated value. The molecular masses of the 30 kDa and 27 kDa polypeptides were determined to be 23769 Da and 21974 Da, respectively. The recombinant Xyn11A polypeptides were named as r33.4 kDa, r23.8 kDa and r22.0 kDa polypeptides (Table 1) on the basis of their molecular masses on mass spectrometry. The N-terminus of all four polypeptides was DTTITQ (SEQ ID NO:20) which suggests different C-terminal processing in the r23.8 kDa and r22.0 kDa polypeptides. The C-terminal processing sites are shown in FIG. 1.

TABLE 1

Characteristics of the purified Nf Xyn11A and the recombinant Xyn11A polypeptides.

| Enzyme | MW SDS-PAGE | MW Mass spect | N-terminus | Sp. act. (nkat/mg) | pI | Half-life 80° C., pH 5 (min) | Half-life 80° C., pH 7 (min) |
|---|---|---|---|---|---|---|---|
| NfXyn11A | 37 | 32.9 | DTTITQ | 15 568 | 8.5 | 32 | 31 |
| Recombinant enzymes | | | | | | | |
| r33.4kDa | 37 | 33.4 | DTTITQ | 16 005 | 8.6 | 13 | 17 |
| r23.8kDa | 30 | 23.8 | DTTITQ | 17 367 | 7.6 | 157 | 95 |
| r22.0kDa | 27 | 22.0 | DTTITQ | 16 950 | 8.2 | 123 | 63 |

The specific activities of the Nf Xyn11A and the recombinant Xyn11A polypeptides were similar on birch xylan substrate (15568-17367 nkat/mg) (Table 1). Also, the pIs of the full-length proteins, Nf Xyn11A and the r33.4 kDa polypeptide were very similar (8.5 vs. 8.6), but they both differed from the value calculated from the amino acid sequence (7.9). The pIs of the r23.8 kDa and r22.0 kDa polypeptides lacking the CBMs were lower than those of the full-length enzymes (7.6 and 8.2 vs. 8.5-8.6).

Example 8

Temperature and pH Dependences of the Purified Xyn11A Xylanases

The pH and temperature optima for xylanase activity were determined by incubating the Xyn11A samples at different pH values (pH 5-8) at temperatures from 60° C. to 80° C. for 60 min. Both at pH 5 (FIG. 5A) and pH 6 (data not shown) the maximal activity was reached at 80° C., and at pH 7 at 70° C. (FIG. 5B). At all pHs the native Nf Xyn11A was the most thermophilic. This was seen especially at pH 8, where the optimum for Nf Xyn11A was at 70° C., and for the recombinant Xyn11A polypeptides at 60° C. (FIG. 5C). The thermostability of the enzymes was determined in the absence of BSA. At 70° C. no reduction in enzyme activity was found even after several hours of incubation. At 80° C.

the reduction was dependent of pH and the enzyme form. At pH 5 the r22.0 kDa and r23.8 kDa polypeptides were more stable (half-lives of 123 min and 157 min) than the full-length Xyn11A polypeptides, r33.4 kDa and Nf Xyn11A (half-lives of 13 min and 32 min) (FIG. 6; Table 1). The enzymes behave similarly also at pH 7, although the half-lives were shorter, 63-95 min for the r22.0 kDa and r23.8 kDa polypeptides, and 17-31 min for the full-length enzymes.

Example 9

Bleaching Experiments Using the Purified Xyn11A Forms

The *N. flexuosa* cultivation medium, the purified native Xyn11A and the recombinant Xyn11A polypeptides produced in *T. reesei* were tested in a single-stage peroxide bleaching with Finnish oxygen-delignified softwood kraft pulp (starting brightness 34% ISO, kappa number 20 and dry matter content 29.9%) at 100 nkat/g pulp dry matter *N. flexuosa* supernatant also 50 nkat/ml). The purified enzymes were supplemented with *T. reesei* culture medium to stabilize the enzymes. The amount of culture medium corresponded to the ratio of thermoxylanase activity and total protein content in the original recombinant *T. reesei* culture media used for enzyme purifications. After these additions the mixtures resembled the enzyme preparations to be used in actual industrial applications. Pulp treatments were carried out at 3% consistency at 80° C. and pH 8 for one hour. Reference pulp was treated similarly without enzyme addition. After enzyme treatments the pulp was washed with distilled water. Chelation was performed by adding EDTA to 0.2% of dry matter and carried out at 3.0% consistency at pH 5 for one hour. Pulp was bleached at 10% pulp consistency at 80° C. for three hours ($H_2O_2$ 3%, NaOH 3%, diethylenetriamine pentaacetic acid 0.2%, $MgSO_4$ 0.5% by volume), after which pulp was acidified with $H_2SO_4$, washed with distilled water and made into paper handsheets.

Reducing sugars in the chelated pulp were analyzed by the dinitrosalicylic acid method. The quality of the bleached and washed pulps was analyzed by determining the kappa number according to the TAPPI Test Method T 236 and viscosity according to the SCAN28 Scandinavian method. Brightness of the handsheets was analysed according to ISO 2470. Peroxide consumption was determined by titration.

In the single-step peroxide bleaching experiment performed with the *N. flexuosa* cultivation medium lignin removal (0.7-1.1 Kappa units depending on enzyme dosage) and brightness increase (1.0-1.1 ISO units) was obtained with no reduction in the pulp strength determined by viscosity (Table 2). The *T. reesei* culture medium increased the brightness by 0.9 ISO units. A further increase of 1.1-1.6 ISO units was obtained with the purified recombinant Xyn11A polypeptides, r33.4 kDa, r23.8 kDa and r22.0 kDa—the r22.0 kDa polypeptide being the least efficient (Table 2).

TABLE 2

Peroxide bleaching with the *N. flexuosa* cultivation medium and the purified recombinant Xyn11A polypeptides.

| Xylanase | Brightness/ Brightness increase (ISO) | Kappa | Viscosity ($dm^3$/kg) | Reducing sugars (% of dry matter) | Peroxide consumption (%) |
|---|---|---|---|---|---|
| *N. flexuosa* medium[a] | 72.9 | 8.3 | 890 | ND | ND |
| *N. flexuosa* medium[b] | 73.0 | 7.9 | 890 | ND | ND |
| Reference | 71.9 | 9.0 | 870 | ND | ND |
| r33.4 kDa | 64.5/+2.4 | 8.8 | ND | 0.30 | 2.3 |
| r23.8 kDa | 64.6/+2.5 | 8.1 | ND | 0.31 | 2.3 |
| r22.0 kDa | 64.1/+2.0 | 8.7 | ND | 0.30 | 2.3 |
| *T. reesei* medium | 63.0/+0.9 | 9.2 | ND | 0.25 | 2.3 |
| Reference | 62.1 | 8.7 | ND | 0.25 | 2.2 |

[a]Enzyme dosage 50 nkat/g pulp dry matter.
[b]Enzyme dosage 100 nkat/g pulp dry matter.

Example 10

Construction of the Expression Cassettes for Heterologous Production of Nf Xyn11A (AM35) and the Truncated Nf Xyn11A (AM24) in *T. reesei*

For production of Nf Xyn11A (AM35) and the truncated Nf Xyn11A (AM24) in *T. reesei* several expression cassettes were constructed that either include a fungal signal sequence or the fungal signal sequence and a variable carrier polypeptide for these two proteins. The am35 lam35* (see below) and am24/am24* (see below) genes were expressed from the *T. reesei* cel7A promoter. The expression cassettes constructed are listed in Table 3 and their general structure is shown in FIG. 6. The Table 3 also includes the other relevant information on the constructs. The promoter, transcription terminator and 3'-flanking sequences were as described in (Karhunen, et al., Mol. Gen. Genet., 241, 515-522, 1993). The gene coding for acetamidase (amdS) was used as a marker in the transformations. The amdS gene was isolated from p3SR2 (Kelly and Hynes, EMBO J., 4, 75-479, 1985). A 3.1 kb SpeI-XbaI fragment was ligated between the cel7A terminator and 3'-flanking region. In addition to these two genes, am35 and am24, with the native codon usage, the following 9 changes were made to codons in some of the constructs (see Table 3), to make the codons more favorable to *T. reesei*: $Gly_{53}$ GGG to GGC, $Ala_{66}$ GCG to GCC, $Gly_{68}$ GGG to GGC, $Arg_{85}$ CGG to CGC, $Gly_{88}$ GGG to GGC, $Gly_{100}$ GGA to GGC, $Arg_{101}$ CGG to CGC, $Arg_{102}$ CGG to CGC and $Val_{104}$ GTG to GTC. The genes including the changes described above were designated as am35* and am24*. The changes made did not change the amino acid sequence encoded by the genes, compared to am35 and am24.

When the full-length *N. flexuosa* Xyn11A was produced, the am35 and am35* genes were included in the expression cassettes either as a 1.3 kb fragment ending at the MluI site about 250 bps after the stop codon or as an exact fusion of the am35 to the cbh1 terminator. The shortened genes, am24 and am24* ended to nucleotide 1091 (FIG. 1) and they were exactly fused to cbh1 terminator including the stop codon. All the genes were fused from the

TABLE 3

The constructs used to express the N. flexuosa am35/am35* gene and the shortened am35/am35* gene (am24/am24*).

| Expr. cassette | Carrier protein | Xylanase gene | Term. fusion | Reference |
|---|---|---|---|---|
| pALK1118 | No carrier (man5A ss) | am35 | Non-exact | Paloheimo et at. (2003) |
| pALK1276 | No carrier (man5A ss) | am24 | Exact | This application |
| pALK1022 | Man5A core/hinge | am35 | Non-exact | Paloheimo et at. (2003) |
| pALK1692 | Man5A core/hinge | am35 | Exact | This application |
| pALK1309 | Man5A core/hinge | am35* | Non-exact | This application |
| pALK1131 | Man5A core/hinge | am24* | Exact | This application |
| pALK1285 | Cel6A CBD/hinge | am35 | Non-exact | Paloheimo et at. (2003) |
| pALK1502 | Cel6A CBD/hinge | am24* | Exact | This application |
| pALK1264 | Man5A fragment | am35 | Non-exact | Paloheimo et at. (2003) |
| pALK1151 | Man5A fragment | am24 | Exact | This application |
| pALK1154 | Man5A fragment | am24* | Exact | This application | sequence encoding the N-terminal $Asp_{44}$ (from nucleotide 432, FIG. 1) to the man5A signal sequence (PALK1118 and pALK1276, man5A nucleotides 1-57) or to a sequence encoding a carrier polypeptide. The carrier polypeptide sequences included the man5A core/hinge encoding sequence (pALK1022, pALK1309, pALK1131 and pALK1692, 1-1359), the sequence encoding a fragment of the man5A core (PALK1264, pALK1151 and pALK1154, 1-681) and the cel6A CBD/hinge (blocks A and B in pALK1285 and pALK1502, 1-306). For the man5A sequence, see Stålbrand, et al., (Appl. Environ. Microbiol., 61, 1090-1097, 1995). For the cel6A sequence, see (Teeri, et al., Gene, 51, 43-52, 1987). A synthetic sequence coding for the dipeptide Lys-Arg, a target of a Kex2-like protease (Calmels, et al., J. Biotechnol., 17, 51-66, 1991) was included in the linkers of all the constructs including the carrier protein (not in the signal sequence constructs pALK1118 and pALK1276). In addition, the linkers of pALK1264, pALK1151 and pALK1154 were preceded by a sequence coding for the amino acids Gly-Gln-Cys-Gly-Gly (SEQ ID NO:22). This additional sequence was included to increase the length of the linker between this non-intact carrier and the recombinant xylanase. An identical sequence, naturally occurring in the Man5A polypeptide, is preceding the xylanase sequence in pALK1022.

Exact fusions between the cel7A promoter and the signal sequences, carrier, linker, xyn11A sequences and terminator were synthesized by PCR. An NruI recognition site ( TCGCGA (SEQ ID NO:24)) was introduced into the Kex2 linker (coded by a sequence CGCGAC AAG CGC (SEQ ID NO:25)) to facilitate the construction of the fusions. The codon CGC was chosen for the arginines in the linker and the third nucleotide of the native codon preceeding the linker was changed to T, when necessary. The modifications made did not change the amino acids encoded by the constructs.

Example 11

Transformation of Trichoderma and Analysis of the Transformants

T. reesei protoplasts were transformed with linear expression cassettes isolated from the vector backbones by EcoRI. The expression cassettes were transformed to T. reesei strain ALKO3620 (Cel5A⁻) and/or to ALKO4468 (Cel5A⁻, Cel7B⁻), see the Table 4. Transformations were performed as in Penttilä, et al. (Gene, 61, 155-164, 1987) with the modifications described in Karhunen, et al. (Mol. Gen. Genet., 241, 515-522, 1993). The transformants were purified on selection plates through single conidia prior to sporulating them on PD. Targeting to the cel7A locus was screened as Cel7A-negative phenotype using Minifold I-SRC 96 dot blotter (Schleicher & Schuell, Dassel, Germany). The monoclonal antibody CI-258 or CI-261 (Aho, et al., Eur. J. Biochem., 200, 643-649, 1991) was used in the detection of Cel7A protein by the ProtoBlot Western blot AP system (Promega). The genotypes of the chosen transformants were confirmed by using Southern blots in which several genomic digests were included and the respective expression cassettes were used as probes. Strains containing a replacement of the cel7A with one copy of the expression cassette were chosen for further studies.

TABLE 4

Xylanase production from single-copy Trichoderma reesei transformants in laboratory scale fermentations.

| Strain | Expression cassette | T. reesei host | Prot. (mg/ml) | Xylanase (nkat/ml) |
|---|---|---|---|---|
| 1. T. reesei host strains | | | | |
| ALKO3620 | No cassette | | 14.4 | 1 490 |
| ALKO4468 | No cassette | | 9.3 | 430 |
| 2. No carrier (Man5a signal sequence): | | | | |
| ALKO4766 | pALK1118 | ALKO4468 | 8.8 | 2 460 |
| RF5724 | pALK1118 | ALKO3620 | 11.3 | 3 870 |
| RF5024 | pALK1276 | ALKO3620 | 7.7 | 31 830 |
| 3. Man5A core/hinge as a carrier | | | | |
| ALK04405 | pALK1022 | ALKO3620 | 12.3 | 14 400 |
| RF5745 | pALK1692 | ALKO3620 | 4.3 | 13 800 |
| RF5510 | pALK1309 | ALKO3620 | 11.9 | 14 600 |
| RF5725 | pALK1131 | ALKO3620 | 14.1 | 45 940 |
| ALK04812 | pALK1131 | ALKO4468 | 12.3 | 42 980 |
| 4. Cel6A CBD (A + B) as a carrier | | | | |
| RF5013 | pALK1285 | ALKO3620 | 7.5 | 10 750 |
| RF5139 | pALK1502 | ALKO3620 | 8.8 | 37 140 |
| 5. Fragment of Man5A as a carrier | | | | |
| ALK04823 | pALK1264 | ALKO4468 | 8.8 | 4 940 |
| RF4861 | pALK1151 | ALKO3620 | 7.8 | 26 400 |
| RF4878 | pALK1154 | ALKO3620 | 9.8 | 29 600 |

Example 12

Production of the AM35 and AM24 Xylanases by Single-copy T. reesei Transformants We have previously shown (Paloheimo, et al., Appl. Environ. Microbiol., 69, 7073-7082, 2003) that when a carrier polypeptide with an intact domain structure was used, higher production level of AM35 was obtained in T.

reesei compared to the constructs without a carrier or with a carrier of non-intact domain structure. Also, the recombinant AM35 proteins had the same thermostability as the xylanase activity in the N. flexuosa cultivation supernatant. The xylanase activities were stable for at least two hours at 70° C., pH 7. The culture supernatants were also found to increase the brightness of pulp in laboratory scale peroxide of kraft pulp at high temperature and pH in the same way as the culture supernatant from N. flexuosa.

Now, the expression cassettes contained either the am35/am35* gene encoding the full-length Xyn11A or a shortened version from it, am24/am24*, encoding the truncated Xyn11A protein. Both these proteins were produced using three different carrier polypeptides and also without a carrier polypeptide (only a fungal signal sequence was included). The carriers had either an intact domain structure as Man5A core/hinge of Cel6A CBD/hinge or a non-intact domain structure as Man5A core/hinge fragment.

The expression cassettes shown in Table 3 (FIG. 6) were isolated from the expression plasmids and transformed to T. reesei ALKO3620 and/or ALKO4468. The transformants containing single-copy replacement of cel7A gene by the expression cassettes were screened for further analysis. Several parallel single-copy strains from each construct were similar in terms of protein and xylanase activity levels analyzed from the culture supernatants of shake flask cultivations. One single-copy representative from each construct was chosen to be cultivated in the fermentor. The culture supernatants from the fermentor cultivations were analysed for the amount of protein and xylanase activities (Table 4).

The results from fermentor cultivations (Table 4) showed that the best xylanase activities were obtained from the T. reesei transformants including the constructs in which the shortened genes, am24 or am24*, were used. The increase in xylanase activity was observed with all the carriers tested and also when no carrier protein was included (e.g. RF5024 vs. RF5724, RF5725 vs. ALKO4405, RF5139 vs. RF5013, RF4861 vs. ALKO4823). The changes made to codons did not have an effect on the xylanase production level (ALKO4405 vs. RF5510 and RF4861 vs. RF4878). Also, similar levels of activity were obtained from the transformant with the construct in which the xylanase gene was fused exactly to the terminator sequence compared to the transformant including the construct in which there was a non-exact fusion of the xylanase gene to the terminator (RF5745 vs. ALKO4405). This similar level of activity was obtained even though, for unknown reason, the level of total protein in the culture supernatant of RF5745 including an exact terminator fusion was lower than in the corresponding transformant with a non-exact terminator fusion. Both the T. reesei host strains used, transformed with the same expression cassette did produce similar amount of activity (RF5725 vs. ALKO4812).

Because the specific activities of the AM35 and AM24 proteins are very similar to each other (Table 1, r33.4 and r23.8 kDa) it can be concluded that shortening of Nonomuraea xylanase gene increases the production level of xylanase in T. reesei. When the carriers with an intact domain structure were used (Man5A core/hinge and Cel6A CBD/hinge), the xylanase activity levels measured from the culture supernatants were over three-fold higher for the constructs in which AM24 was produced compared to the corresponding constructs for AM35. For the constructs in which no carrier polypeptide was included or the carrier was a fragment of Man5A (no intact domain structure), the increase in xylanase activity in the culture supernatant was even higher, from over 5- to over 10-fold. Thus, even with no carrier or by using carrier having a non-optimal structure, the yield of the bacterial xylanase could be increased to a surprisingly high level when a shortened xylanase gene was expressed in T. reesei.

Increases in the levels of xylanase activity were also observed in the shake flasks cultivations. When no carrier polypeptide was used, the increase in xylanase activity (RF5024 compared to RF5724) was about 2.8-fold and reached 4900 nkat/ml. When Man5A core/hinge was used as a carrier (RF5725 compared to ALKO4405), the increase in activity was about 2.7-fold (RF5725 produced about 21 000 nkat/ml). By using the Cel6A CBD carrier (RF5139 vs. RF5013) the increase in activity was even higher, about 5.6-fold. This high increase was due to the low level of activity in shake flasks from the strains producing AM35 with the Cel6A CBD carrier polypeptide (e.g. RF5013 produced about 3000 nkat/ml, and the activity from RF5139 cultivations was about 16 800 nkat/ml).

The FIG. 8 shows the AM24 xylanase product from a T. reesei transformant (Cel6A CBD carrier was used). In addition to the protein having the expected molecular mass, also a xylanase form having a lower molecular mass (corresponding to r22.0 kDa) can be detected from the culture supernatant. This form is due to a proteolytic cleavage of the AM24 protein.

Example 13

The Use of the T. reesei Culture Supernatants Containing the Recombinant Truncated Nf Xyn11A (AM24) Xylanase in Bleaching Culture supernatant from a T. reesei transformant producing the recombinant truncated Xyn11A protein (AM24) was tested in bleaching of kraft pulp (Scandinavian birch and pine). The results obtained are shown on Tables 5 and 6. The same brightness could be obtained with lower $ClO_2$ consumption in both the bleaching experiments when AM24 was used compared to the reference bleaching without a treatment with the xylanase preparation.

TABLE 5

Thermoxylanase in bleaching of birch mill kraft pulp

| | | Bleaching no | | | | |
| --- | --- | --- | --- | --- | --- | --- |
| | | 1717 Ref. | 1718 | 1719 | 1720 | 1721 |
| X-stage | Enzyme | | | | | |
| Consist. 8% | Enzyme dosage, l/tp | no | 0.3 | 0.15 | 0.3 | 0.15 |
| Temp. 82° C. | $H_2SO_4$, kg/tp (for pH adjustment) | 6.9 | 7.3 | 7.3 | 9.9 | 9.9 |
| Time 20 min | pH start/final | 7.0/7.6 | 7.0/7.9 | 7.0/7.9 | 6.0/6.3 | 6.0/6.3 |
| | | | no washing after enzyme treatment | | | |

TABLE 5-continued

Thermoxylanase in bleaching of birch mill kraft pulp

| | | Bleaching no | | | | |
|---|---|---|---|---|---|---|
| | | 1717 Ref. | 1718 | 1719 | 1720 | 1721 |
| D0-stage | | | | | | |
| Consist. 9% | ClO$_2$ dosage, aCl kg/tp | 47.0 | 41.0 | 41.0 | 41.0 | 41.0 |
| Temp. 70° C. | ClO$_2$ consumpt., aCl kg/tp | 47.0 | 41.0 | 41.0 | 41.0 | 41.0 |
| Time 30 min | final pH | 2.8 | 2.6 | 3.0 | 2.4 | 2.5 |
| (EO)-stage | NaOH dosage, kg/t | 21.0 | 21.0 | 21.0 | 21.0 | 21.0 |
| Consist. 10% | final pH | 10.3 | 10.2 | 10.3 | 10.3 | 10.3 |
| Temp. 85° C. | Brightness, % | 79.3 | 79.1 | 78.9 | 80.3 | 79.6 |
| Time 60 min | Kappa number | 2.5 | 2.5 | 2.9 | 2.4 | 2.6 |
| 4 bar O$_2$ | XD(EO) yield, % | 93.4 | 93.2 | 93.9 | 91.3 | 92.5 |
| D2-stage | ClO$_2$ dosage, aCl kg/tp | 17.0 | 15.0 | 15.0 | 14.0 | 14.5 |
| Consist 9% | ClO$_2$ consumpt., aCl kg/tp | 15.6 | 14.4 | 14.4 | 13.2 | 13.2 |
| Temp 75° C. | NaOH kg/tp (for pH adjustment) | 2.5 | 2.2 | 2.2 | 2.1 | 2.1 |
| Time 110 min | final pH | 4.3 | 4.6 | 4.6 | 4.3 | 4.3 |
| | Brightness, % | 90.1 | 90.2 | 90.1 | 90.7 | 90.3 |
| | Kappa number | 0.6 | 0.6 | ND | ND | ND |
| | D2-yield, % | 98.7 | 98.6 | 97.8 | 99.0 | 98.5 |
| | Total bleaching yield, % | 92.2 | 91.9 | 91.8 | 90.4 | 91.1 |
| | Tot. ClO$_2$ dosage, aCl kg/tp | 64.0 | 56.0 | 56.0 | 55.0 | 55.5 |
| | Tot. ClO$_2$ consumpt, aCl kg/tp | 62.6 | 55.4 | 55.4 | 54.2 | 54.2 |
| | Tot. NaOH kg/tp | 23.5 | 23.2 | 23.2 | 23.1 | 23.1 |
| | Tot. H$_2$SO$_4$, kg/tp | 6.9 | 7.3 | 7.3 | 9.9 | 9.9 |

The sequence used was X/D-EO-D, the kappa number of the original birch kraft pulp used (from handsheet) was 14.4 and brightness 44.1%. The activity of the enzyme preparation used was 187 000 nkat/ml (measured at pH 7, 70° C. using 5 min reaction time).
ND = not determined.
All the pH values were measured from pulp slurry at the reaction temperature. The pulp samples were acidified to pH 4.5 with SO$_2$-water before the sheet preparation to eliminate the residual chemicals. The pulp properties were tested according to ISO standard methods: brightness ISO 2470 (split pulp sheet), kappa numer ISO 302.
tp = ton of pulp.
aCl = active chlorine.

TABLE 6

Thermoxylanase in bleaching of softwood kraft pulp.

| | | Bleaching no | | |
|---|---|---|---|---|
| | | 1627 Ref. | 1692 | 1698 |
| X-stage | Enzyme | | | |
| Consist. 8% | Enzyme dosage, l/tp | no | 0.3 | 0.3 |
| Temp. 70° C. | H$_2$SO$_4$, kg/tp (for pH adjustment) | 2.7 | 2.7 | 2.7 |
| Time 60 min | pH start/final | 7.0/7.4 | 7.0/7.3 | 7.0/7.3 |
| D0-stage | | | | |
| Consist. 9% | ClO$_2$ dosage, aCl kg/tp | 60.0 | 54.0 | 54.0 |
| Temp. 50° C. | ClO$_2$ consumpt., aCl kg/tp | 60.0 | 54.0 | 54.0 |
| Time 45 min | final pH | 1.7 | 1.9 | 1.9 |
| E1-stage | NaOH dosage, kg/t | 27.0 | 27.0 | 27.0 |
| Consist. 10% | final pH | 10.9 | 11.1 | 11.1 |
| Temp. 60° C. | Brightness, % | 49.5 | 49.6 | 49.4 |
| Time 60 min | Kappa number | 6.1 | 6.2 | 6.5 |
| D1-stage | ClO$_2$ dosage, aCl kg/tp | 24.5 | 20.0 | 20.0 |
| Consist 10% | ClO$_2$ consumpt., aCl kg/tp | 24.5 | 19.8 | 20.0 |
| Temp 70° C. | NaOH kg/tp (for pH adjustment) | 3.4 | 3.0 | 2.7 |
| Time 240 min | final pH | 3.6 | 4.2 | 4.1 |
| | Brightness, % | 78.9 | ND | 77.2 |
| | Kappa number | 1.8 | ND | ND |
| E2-stage | NaOH dosage, kg/t | 8.0 | 8.0 | 8.0 |
| Consist. 10% | final pH | 10.6 | 10.6 | 10.6 |
| Temp. 70° C. | Brightness, % | ND | 77.5 | ND |
| Time 60 min | Kappa number | ND | 1.5 | ND |

TABLE 6-continued

Thermoxylanase in bleaching of softwood kraft pulp.

| | | Bleaching no | | |
|---|---|---|---|---|
| | | 1627 Ref. | 1692 | 1698 |
| D2-stage | ClO$_2$ dosage, aCl kg/tp | 9.0 | 8.0 | 9.5 |
| Consist. 10% | ClO$_2$ consumpt., aCl kg/tp | 7.9 | 7.6 | 9.3 |
| Temp. 70° C. | NaOH kg/tp (for pH adjustment) | 1.1 | 0.9 | 1.1 |
| Time 240 min | final pH | 4.6 | 4.4 | 4.2 |
| | Brightness, % | 90.0 | 89.4 | 89.9 |
| | Kappa number | 0.7 | 0.7 | 0.6 |
| | Viscosity ml/g | 1030.0 | ND | 1050.0 |
| | Tot. ClO$_2$, aCl kg/tp | 93.5 | 82.0 | 83.5 |
| | Tot. NaOH kg/tp | 39.5 | 38.9 | 38.8 |
| | Tot. H$_2$SO$_4$, kg/tp | 2.7 | 2.7 | 2.7 |

Sequence X/D-E-D-E-D was used. The Kappa number of the original pulp was 28.9 (from handsheet), brightness 28.2% and viscosity 1180 ml/g. The activity of the enzyme preparation used was 187 000 nkat/ml (measured at pH 7, 70° C., 5 min reaction time).
ND = not done.
All the pH values were measured from pulp slurry at the reaction temperature. The pulp samples were acidified to pH 4.5 with SO$_2$-water before the sheet preparation to eliminate the residual chemicals. The pulp properties were tested according to ISO standard methods: brightness ISO 2470 (split pulp sheet), kappa numer ISO 302, viscosity ISO 5351/1.
tp = ton of pulp.
aCl = active chlorine.

Example 14

The Use of the *T. reesei* Culture Supernatants Containing the Recombinant AM24 Xylanase in Feed Application Two feeding trials with broilers were performed with the AM24 xylanase preparation. The results from the trials demonstrated a good effect of AM24 in poultry. The bodyweight in wheat-barley based diet was increased, compared to un-supplemented control birds, by 3.4% and in wheat and soy bean meal by 3.1-3.7%. Also, nutrient digestibility was significantly increased as measured by feed conversion rate. The AM24 xylanase preparation was at least as effective as the *T. reesei* XYNII (XYLII) used for years in animal nutrition. The advantage of the AM24 xylanase is the high heat stability compared to e.g. *T. reesei* XYNII (XYLII) which is a great improvement for several feed production procedures.

Example 15

The Production of Nf Xyn10A (AM50) and Two Truncated Forms of Nf Xyn10A in *T. reesei*

The gene coding for the Nf Xyn10A (AM50) xylanase (am50 or Nf xyn10A; EMBL accession no AJ508953) was isolated from a lambda ZAP Express® library prepared from partially digested (Sau3A) and size-fractionated *Actinomadura* (*Nonomuraea*) *flexuosa* DSM43186 (ATCC35864) chromosomal DNA as described in U.S. Pat. No. 6,300,113. The nucleotide sequence of the gene and the deduced amino acid sequence are shown in FIG. 2. Three expression cassettes (FIG. 9) are constructed for production of the full-length AM50 protein (amino acids A$_{45}$-A$_{492}$ from FIG. 2) and two truncated forms from it, the core (A$_{45}$-N$_{345}$) and the core/linker missing all the three subdomains from the tail (A$_{45}$-S$_{367}$). Also, constructs could be made that encode Xyn10A polypeptides deficient in only the γ-subdomain or the γ- and β-subdomains of the tail. The estimated molecular masses of the different polypeptides would be (from the N-terminal A$_{45}$, without any added sugar moieties): core 34.0 kDa, core-linker 35.9 kDa, core-linker-α-subdomain of the tail 40.6 kDa, core-linker-α+β-subdomains of the tail 44.8 kDa, core-linker-α+β+γ-subdomains of the tail (full length mature protein) 49.1 kDa. The standard molecular biology methods, PCR reactions and annealing of oligonucleotides are used to make exact fusions between different sequences encoding: the cbh1 promoter, cel6A signal sequence and sequence encoding Cel6A CBD (A+B), Kex2 site (RDKR), sequence encoding Nf xyn10A (core or core/hinge or the full-length protein) and cbh1 terminator. The restriction sites at the end and the beginning of the fragments to be fused are included in the oligonucleotides to enable easy construction of the fusions. Finally, the amdS marker gene and the cbh1 3'-flanking region will be included as in the constructs made for expressing the am35/am24 genes. The expression cassettes are isolated from the vector backbones using EcoRI digestion and they are transformed to *T. reesei* host strain. The same methods for the transformation, handling and selection of the transformants will be used as in construction of the strains producing Nf Xyn11A: the transformants are purified through single conidia and they are screened in shake flask cultivations by measuring the xylanase activity from the cultivation supernatants. The single-copy transformants in which the expression cassette is replacing the cbh1 locus will be chosen basing on the results on xylanase production level and Southern blot analysis of the genomes. The increased xylanase production from the strains producing the truncated forms of the Nf Xyn10A protein, compared to the strains producing the full length Nf Xyn10A is shown by using activity assays, SDS-PAGE and Western blot methods.

The culture supernatant(s) are used in the application tests, both for the bleaching of kraft pulp and feed applications, to show the effect of the xylanase(s).

What is claimed is:

1. A method for increasing the production level of *Nonomuraea flexuosa* xylanase Xyn11A (Nf Xyn11A) in a filamentous fungal host, said method comprising:
   expressing a DNA construct comprising a DNA sequence comprising DNA encoding the amino acid sequence of a truncated form of the Nf Xyn11A mature protein in a filamentous fungal host, said amino acid sequence of said truncated form of said mature protein consisting of the amino acid sequence of SEQ ID NO: 12, and
   secreting said truncated form of said Nf Xyn11A,
   wherein said production level obtained using said DNA construct, when measured as an increase of activity from the culture media of single copy transformants, is higher than the production level obtained using a corresponding DNA construct that is identical to said DNA construct encoding said truncated form, except that it comprises a DNA sequence encoding the sequence of the full length Nf Xyn11A xylanase (SEQ ID NO: 11) instead of a DNA sequence encoding said truncated form.

2. The method according to claim 1, wherein said DNA sequence that is expressed further comprises a sequence encoding a carrier polypeptide.

3. The method according to claim 2, wherein said carrier polypeptide comprises one or more regions or domains of a secretable filamentous fungi carbohydrate degrading enzyme.

4. The method according to claim 2, wherein said carrier polypeptide is the *T. reesei* mannanase (Man5A) core.

5. The method according to claim 2, wherein said carrier polypeptide is the *T. reesei* mannanase (Man5A) core/hinge region.

6. The method according to claim 2, wherein said carrier polypeptide is the *T. reesei* cellobiohydrolase 2 (Ce16A) carbohydrate binding domain (CBD), said Ce16A CBD plus a hinge region, or said Ce16A plus duplicate hinge regions.

7. The method according to claim 1, wherein said DNA sequence is expressed under the control of a *Trichoderma* promoter.

8. The method according to claim 7, wherein said *Trichoderma* promoter is the *T. reesci* cellobiohydrolase 1 gene (cbh1 or ce17A) promoter.

9. The method according to claim 1 wherein said DNA sequence is expressed under the control of an *Aspergillus* promoter.

10. The method according to claim 1, wherein said higher production level is at least 2 times higher than the production level achieved with said full length xylanase DNA construct.

11. A method for increasing the production level of *Nonomuraea flexuosa* xylanase Xyn11A (Nf Xyn11A) in a filamentous fungal host, said method comprising:
introducing a DNA construct into a filamentous fungal host, said DNA construct comprising (a) a DNA sequence comprising DNA encoding the amino acid sequence of a truncated form of the Nf Xyn11A mature protein, said amino acid sequence of said truncated form of said mature protein consisting of the amino acid sequence of SEQ ID NO: 12, and (b) regulatory sequences for expression of said DNA sequence,
expressing said DNA sequence and secreting said truncated form of said Nf Xyn11A under the control of said regulatory sequences,
wherein said regulatory sequences are derived from filamentous fungi and comprise a promoter sequence, a signal sequence, and a terminator sequence, and
wherein said production level obtained using said DNA construct, when measured as an increase of activity from the culture media of single copy transformants, is higher than the production level obtained using a corresponding DNA construct that is identical to said DNA construct encoding said truncated form, except that it comprises a DNA sequence encoding the sequence of the full length Nf Xyn11A xylanase (SEQ ID NO: 11) instead of a DNA sequence encoding said truncated form.

12. The method according to claim 11, wherein said regulatory sequences further comprise a sequence encoding a carrier polypeptide.

13. The method according to claim 12, wherein said carrier polypeptide comprises one or more regions or domains of a secretable filamentous fungi carbohydrate degrading enzyme.

14. The method according to claim 12, wherein said carrier polypeptide is the *T. reesei* mannanase (Man5A) core.

15. The method according to claim 12, wherein said carrier polypeptide is the *T. reesei* mannanase (Man5A) core/hinge region.

16. The method according to claim 12, wherein said carrier polypeptide is the *T. reesei* cellobiohydrolase 2 (Cel6A) carbohydrate binding domain (CBD), said Cel6A CBD plus a hinge region, or said Cel6A plus duplicate hinge regions.

17. The method according to claim 11, wherein said promoter is a *Trichoderma* promoter.

18. The method according to claim 17, wherein said *Trichoderma* promoter is the *T. reesei* cellobiohydrolase 1 gene (cbh1 or cel7A) promoter.

19. The method according to claim 11, wherein said promoter is an *Aspergillus* promoter.

20. The method according to claim 11, wherein said higher production level is at least 2 times higher than the production level achieved with said full length xylanase DNA construct.

21. A DNA construct comprising (a) a DNA sequence that comprises DNA encoding the amino acid sequence of a truncated form of the *Nonomuraea flexuosa* xylanase Xyn11A (Nf Xyn11A) mature protein, said amino acid sequence of said truncated form consisting of the amino acid sequence of SEQ ID NO: 12, and (b) regulatory sequences for expression of said DNA sequence,
wherein said regulatory sequences are derived from filamentous fungi and comprise a promoter sequence, a signal sequence, and a terminator sequence.

22. The DNA construct according to claim 21, wherein said DNA sequence further encodes a carrier protein.

23. The DNA construct according to claim 22, wherein said carrier polypeptide encodes one or more regions or domains of a filamentous fungi secretable carbohydrate degrading enzyme.

24. The DNA construct according to claim 22, wherein said carrier polypeptide is the *T. reesei* mannanase (Man5A) core.

25. The DNA construct according to claim 22, wherein said carrier polypeptide is the *T. reesei* mannanase (Man5A) core/hinge region.

26. The DNA construct according to claim 22, wherein said carrier polypeptide is the *T. reesei* cellobiohydrolase 2 (Cel6A) carbohydrate binding domain (CBD), said Cel6A CBD plus a hinge region, or said Cel6A plus duplicate hinge regions.

27. The DNA construct according to claim 21, wherein said promoter is a *Trichoderma* promoter.

28. The DNA construct according to claim 27, wherein said *Trichoderma* promoter is the *T. reesei* cellobiohydrolase 1 gene (cbh1 or cel7A) promoter.

29. The DNA construct according to claim 21, wherein said promoter is an *Aspergillus* promoter.

30. The DNA construct according to claim 21, wherein by expressing said DNA construct in a filamentous fungal host the production level is at least two times higher than the production level achieved with a corresponding DNA construct that is identical to said DNA construct encoding said truncated form, except that it comprises a DNA sequence encoding the sequence of the full length NE Xyn11A xylanase (SEQ ID NO: 11) instead of a DNA sequence encoding said truncated form.

31. The method of claim 1 or claim 11, wherein said host is *Trichoderma*.

32. The method of claim 31, wherein said host is *T. reesei*.

* * * * *

SEQUENCE LISTING

<160> NUMBER OF SEQ ID NOS: 25

<210> SEQ ID NO 1
<211> LENGTH: 1375
<212> TYPE: DNA
<213> ORGANISM: Nonomuraea flexuosa
<220> FEATURE:
<223> OTHER INFORMATION: Nf xyn11A nucleotide sequence (AJ508952), the coding region is from nt 303 to nt 1337

<400> SEQUENCE: 1

```
cccgggtatt catgtgaatg attagcaaca gttatgttac ggagatattt ctgagagtgt      60
tgacaggtcg tgaagtcggt ccgatacttt cgagctagct ccgatagttt tcgatacgcc     120
ggcacatcga gcacgtcgga cgagtcacgc gccacgtcgg ttttccgccg cacgccgcgc     180
agagcggccg gagaaccccc gcgtgtccgg ggcatcggtg ccggtccgtc gttcgccgcc     240
gaccgcgcgc cgggtcgcga cacgccagcc cccatcggcc cttcttcacg aggaagccgt     300
acatgaacga accctcacc atcacgcagg ccaggcgccg cagacgcctc ggcctccggc     360
gcatcgtcac cagtgccttc gccctggcac tcgccatcgc cggtgcgctg ctgcccggca     420
cggcccacgc cgacaccacc atcacccaga accagaccgg gtacgacaac ggctacttct     480
actcgttctg gaccgacgcg cccgggaccg tctccatgac cctccactcg gcggcagct     540
acagcacctc gtggcggaac accgggaact tcgtcgccgg caagggctgg tccaccggcg     600
gacggcggac cgtgacctac aacgcctcct tcaacccgtc gggtaacgcc tacctcacgc     660
tctacggctg gaccaggaac ccgctcgtcg agtactacat cgtcgagagc tggggcacct     720
accgcccac cggcacctac aagggcaccg tcaccaccga cggcggcacg tacgacatct     780
acgagacctg gcggtacaac gcgccgtcca tcgagggcac ccggaccttc cagcagttct     840
ggagcgtccg gcagcagaag cggaccagcg gcaccatcac catcggcaac cacttcgacg     900
cctgggcccg cgccggcatg aacctgggca gccacgacta ccagatcatg gcgaccgagg     960
gctaccagag cagcggtagc tccaccgtct ccatcagcga gggtggcaac cccggcaacc    1020
cgggtaaccc cggcaaccccc ggcaaccccg gtaacccggg taaccccggc ggtggctgcg    1080
tcgcgaccct ctccgccggc cagcagtgga gcgaccgcta caacctcaac gtctcggtca    1140
gcggctcgaa caactggacg gtccggatgg acgtgcccta cccggcccgc atcatcgcca    1200
cctggaacat ccacgcccag tggcccgagt cccaggtgct catcgccaga cccaacggca    1260
acggcaacaa ctggggcgtg acgatccagc acaacggcaa ctggacctgg ccgacggtca    1320
cctgtaccgc gaactgagtt cccgccccca aggtggcgc ggcggctccc ggccg          1375
```

<210> SEQ ID NO 2
<211> LENGTH: 906
<212> TYPE: DNA
<213> ORGANISM: Nonomuraea flexuosa
<220> FEATURE:
<223> OTHER INFORMATION: am35, Nf xyn11A coding region for the mature Nf Xyn11A (AM35) protein

<400> SEQUENCE: 2

```
gacaccacca tcacccagaa ccagaccggg tacgacaacg gctacttcta ctcgttctgg      60
accgacgcgc ccgggaccgt ctccatgacc ctccactcgg cggcagcta cagcacctcg     120
tggcggaaca ccgggaactt cgtcgccggc aagggctggt ccaccggcgg acggcggacc     180
gtgacctaca acgcctcctt caacccgtcg ggtaacgcct acctcacgct ctacggctgg     240
```

```
accaggaacc cgctcgtcga gtactacatc gtcgagagct ggggcaccta ccggcccacc    300
ggcacctaca agggcaccgt caccaccgac ggcggcacgt acgacatcta cgagacctgg    360
cggtacaacg cgccgtccat cgagggcacc cggaccttcc agcagttctg gagcgtccgg    420
cagcagaagc ggaccagcgg caccatcacc atcggcaacc acttcgacgc ctgggcccgc    480
gccggcatga acctgggcag ccacgactac cagatcatgg cgaccgaggg ctaccagagc    540
agcggtagct ccaccgtctc catcagcgag ggtggcaacc ccggcaaccc gggtaacccc    600
ggcaaccccg gcaaccccgg taacccgggt aaccccggcg gtggctgcgt cgcgacccta    660
tccgccggcc agcagtggag cgaccgctac aacctcaacg tctcggtcag cggctcgaac    720
aactggacgg tccggatgga cgtgccctac ccggcccgca tcatcgccac ctggaacatc    780
cacgcccagt ggcccgagtc ccaggtgctc atcgccagac ccaacggcaa cggcaacaac    840
tggggcgtga cgatccagca caacggcaac tggacctggc cgacggtcac ctgtaccgcg    900
aactga                                                                906

<210> SEQ ID NO 3
<211> LENGTH: 663
<212> TYPE: DNA
<213> ORGANISM: Nonomuraea flexuosa
<220> FEATURE:
<223> OTHER INFORMATION: am24, shortened form of am35, includes a STOP
      codon

<400> SEQUENCE: 3
gacaccacca tcacccagaa ccagaccggg tacgacaacg gctacttcta ctcgttctgg     60
accgacgcgc ccgggaccgt ctccatgacc ctccactcgg gcggcagcta cagcacctcg    120
tggcggaaca ccgggaactt cgtcgccggc aagggctggt ccaccggcgg acggcggacc    180
gtgacctaca cgcctccctt caacccgtcg ggtaacgcct acctcacgct ctacggctgg    240
accaggaacc cgctcgtcga gtactacatc gtcgagagct ggggcaccta ccggcccacc    300
ggcacctaca agggcaccgt caccaccgac ggcggcacgt acgacatcta cgagacctgg    360
cggtacaacg cgccgtccat cgagggcacc cggaccttcc agcagttctg gagcgtccgg    420
cagcagaagc ggaccagcgg caccatcacc atcggcaacc acttcgacgc ctgggcccgc    480
gccggcatga acctgggcag ccacgactac cagatcatgg cgaccgaggg ctaccagagc    540
agcggtagct ccaccgtctc catcagcgag ggtggcaacc ccggcaaccc gggtaacccc    600
ggcaaccccg gcaaccccgg taacccgggt aaccccggcg gtggctgcgt cgcgacccta    660
taa                                                                  663

<210> SEQ ID NO 4
<211> LENGTH: 906
<212> TYPE: DNA
<213> ORGANISM: Nonomuraea flexuosa
<220> FEATURE:
<223> OTHER INFORMATION: am35*, like am35 but 9 codons are changed in
      the sequence. See Example 10 (the changes do not alter the
      encoded amino acid
      sequence)

<400> SEQUENCE: 4
gacaccacca tcacccagaa ccagaccggc tacgacaacg gctacttcta ctcgttctgg     60
accgacgccc ccggcaccgt ctccatgacc ctccactcgg gcggcagcta cagcacctcg    120
tggcgcaaca ccggcaacttc gtcgccggc aagggctggt ccaccggcgg ccgccgcacc    180
```

-continued

```
gtcacctaca acgcctcctt caacccgtcg ggtaacgcct acctcacgct ctacggctgg     240
accaggaacc cgctcgtcga gtactacatc gtcgagagct ggggcaccta ccggcccacc     300
ggcacctaca agggcaccgt caccaccgac ggcggcacgt acgacatcta cgagacctgg     360
cggtacaacg cgccgtccat cgagggcacc cggaccttcc agcagttctg gagcgtccgg     420
cagcagaagc ggaccagcgg caccatcacc atcggcaacc acttcgacgc ctgggcccgc     480
gccggcatga acctgggcag ccacgactac cagatcatgg cgaccgaggg ctaccagagc     540
agcggtagct ccaccgtctc catcagcgag ggtggcaacc ccggcaaccc gggtaacccc     600
ggcaaccccg gcaaccccgg taacccgggt aaccccggcg gtggctgcgt cgcgaccctc     660
tccgccggcc agcagtggag cgaccgctac aacctcaacg tctcggtcag cggctcgaac     720
aactggacgt ccggatgga cgtgccctac ccggcccgca tcatcgccac ctggaacatc     780
cacgcccagt ggcccgagtc ccaggtgctc atcgccagac ccaacggcaa cggcaacaac     840
tggggcgtga cgatccagca caacggcaac tggacctggc cgacggtcac ctgtaccgcg     900
aactga                                                                906
```

<210> SEQ ID NO 5
<211> LENGTH: 663
<212> TYPE: DNA
<213> ORGANISM: Nonomuraea flexuosa
<220> FEATURE:
<223> OTHER INFORMATION: am24*, like am24 but 9 codons are changed in
      the sequence like in am35* (See Example 10)

<400> SEQUENCE: 5

```
gacaccacca tcacccagaa ccagaccggc tacgacaacg ctacttctta ctcgttctgg      60
accgacgccc ccggcaccgt ctccatgacc ctccactcgg gcggcagcta cagcacctcg     120
tggcgcaaca ccggcaactt cgtcgccggc aagggctggt ccaccggcgg ccgccgcacc     180
gtcacctaca acgcctcctt caacccgtcg ggtaacgcct acctcacgct ctacggctgg     240
accaggaacc cgctcgtcga gtactacatc gtcgagagct ggggcaccta ccggcccacc     300
ggcacctaca agggcaccgt caccaccgac ggcggcacgt acgacatcta cgagacctgg     360
cggtacaacg cgccgtccat cgagggcacc cggaccttcc agcagttctg gagcgtccgg     420
cagcagaagc ggaccagcgg caccatcacc atcggcaacc acttcgacgc ctgggcccgc     480
gccggcatga acctgggcag ccacgactac cagatcatgg cgaccgaggg ctaccagagc     540
agcggtagct ccaccgtctc catcagcgag ggtggcaacc ccggcaaccc gggtaacccc     600
ggcaaccccg gcaaccccgg taacccgggt aaccccggcg gtggctgcgt cgcgaccctc     660
taa                                                                   663
```

<210> SEQ ID NO 6
<211> LENGTH: 1864
<212> TYPE: DNA
<213> ORGANISM: Nonomuraea flexuosa
<220> FEATURE:
<223> OTHER INFORMATION: Nf xyn10A nucleotide sequence (AJ508953), the
      coding region is from nt 194 to nt 1672

<400> SEQUENCE: 6

```
ttcggcagcc tattgacaaa tttcgtgaat gtttcccaca cttgctctgc agacggcccc      60
gccgatcatg ggtgcaccgg tcggcgggac cgtgctccga cgccattcgg gggtgtgcgc     120
ctgcgggcgc ggcgtcgatc ccgcggggac tcccgcggtt ccctttccgt gtccctctaa     180
tggaggctca ggcatgggcg tgaacgcctt ccccagaccc ggagctcggc ggttcaccgg     240
```

```
cgggctgtac cgggccctgg ccgcggccac ggtgagcgtg gtcggcgtgg tcacggccct    300
gacggtgacc cagcccgcca gcgccgcggc gagcacgctc gccgagggtg ccgcgcagca    360
caaccggtac ttcggcgtgg ccatcgccgc gaacaggctc aacgactcgg tctacaccaa    420
catcgcgaac cgcgagttca actcggtgac ggccgagaac gagatgaaga tcgacgccac    480
cgagccgcag caggggcggt tcgacttcac ccaggccgac cggatctaca actgggcgcg    540
ccagaacggc aagcaggtcc gcggccacac cctggcctgg cactcgcagc agccgcagtg    600
gatgcagaac ctcagcggcc aggcgctgcg ccaggcgatg atcaaccaca tccagggggt    660
catgtcctac taccggggca agatcccgat ctgggacgtg gtgaacgagg cgttcgagga    720
cggcaactcc ggccgccggc gcgactccaa cctccagcgc accggtaacg actggatcga    780
ggtcgcgttc cgcaccgccc gccaggcgga ccccctcggcc aagctctgct acaacgacta    840
caacatcgag aactggaacg cggccaagac ccaggcggtc tacaacatgg tgcgggactt    900
caagtcccgc ggcgtgccca tcgactgcgt gggcttccag tcgcacttca acagcggtaa    960
cccgtacaac ccgaacttcc gcaccaccct gcagcagttc gcggccctcg gcgtggacgt   1020
cgaggtcacc gagctggaca tcgagaacgc cccggcccag acctacgcca gcgtgatccg   1080
ggactgcctg ccgtggacc gctgcaccgg catcaccgtc tggggtgtcc gcgacagcga   1140
ctcctggcgc tcgtaccaga acccgctgct gttcgacaac aacggcaaca agaagcaggc   1200
ctactacgcg gtgctcgacg ccctgaacga gggctccgac gacggtggcg gcccgtccaa   1260
cccgccggtc tcgccgccgc cggggtggcgg ttccgggcag atccggggcg tggcctccaa   1320
ccggtgcatc gacgtgccga acggcaacac cgccgacggc acccaggtcc agctgtacga   1380
ctgccacagc ggttccaacc agcagtgac ctacacctcg tccggtgagt tccgcatctt   1440
cggcaacaag tgcctggacg cgggcggctc cagcaacggt gcggtggtcc agatctacag   1500
ctgctggggc ggcgccaacc agaagtggga gctccgggcc gacggcacca tcgtgggcgt   1560
gcagtccggg ctgtgcctcg acgcggtggg tggcggcacc ggcaacggca cgcggctgca   1620
gctctactcc tgctggggcg caacaacca gaagtggtcc tacaacgcct gatccccggc   1680
tgatcgaccc tagttgaggc cgcctccggt acggcaccgc cgtaccggag gcggtcccct   1740
gttcgtccag gacggaagga ccggtctgag caggcgcggc gatcgggcac catggtggga   1800
ggcacgaaag cgggagggg tcgcatgccg cgagtccggg aagtggaggt gttcctccac   1860
ctga                                                                1864
```

<210> SEQ ID NO 7
<211> LENGTH: 1347
<212> TYPE: DNA
<213> ORGANISM: Nonomuraea flexuosa
<220> FEATURE:
<223> OTHER INFORMATION: am50, Nf xyn10A coding region for the mature
   Nf Xyn10A (AM50) protein

<400> SEQUENCE: 7

```
gcggcgagca cgctcgccga gggtgccgcg cagcacaacc ggtacttcgg cgtggccatc      60
gccgcgaaca ggctcaacga ctcggtctac accaacatcg cgaaccgcga gttcaactcg    120
gtgacggccg agaacgagat gaagatcgac gccaccgagc cgcagcaggg gcggttcgac    180
ttcacccagg ccgaccggat ctacaactgg gcgcgccaga acggcaagca ggtccgcggc    240
cacaccctgg cctggcactc gcagcagccg cagtggatgc agaacctcag cggccaggcg    300
ctgcgccagg cgatgatcaa ccacatccag ggggtcatgt cctactaccg gggcaagatc    360
```

-continued

```
ccgatctggg acgtggtgaa cgaggcgttc gaggacggca actccggccg ccggcgcgac    420
tccaacctcc agcgcaccgg taacgactgg atcgaggtcg cgttccgcac cgcccgccag    480
gcggacccct cggccaagct ctgctacaac gactacaaca tcgagaactg aacgcggcc     540 aagacccagg cggtctacaa catggtgcgg gacttcaagt cccgcggcgt gcccatcgac    600
tgcgtgggct ccagtcgca cttcaacagc ggtaacccgt acaacccgaa cttccgcacc    660
accctgcagc agttcgcggc cctcggcgtg gacgtcgagg tcaccgagct ggacatcgag    720
aacgccccgg cccagaccta cgccagcgtg atccgggact gcctggccgt ggaccgctgc    780
accggcatca ccgtctgggg tgtccgcgac agcgactcct ggcgctcgta ccagaacccg    840
ctgctgttcg acaacaacgg caacaagaag caggcctact acgcggtgct cgacgccctg    900
aacgagggct ccgacgacgg tggcggcccg tccaacccgc cggtctcgcc gccgcgggt    960 ggcggttccg ggcagatccg gggcgtggcc tccaaccggt gcatcgacgt gccgaacggc   1020
aacaccgccg acggcaccca ggtccagctg tacgactgcc acagcggttc caaccagcag   1080
tggacctaca cctcgtccgg tgagttccgc atcttcggca caagtgcct ggacgcgggc    1140 ggctccagca acggtgcggt ggtccagatc tacagctgct ggggcggcgc caaccagaag   1200
tgggagctcc gggccgacgg caccatcgtg ggcgtgcagt ccgggctgtg cctcgacgcg   1260
gtgggtggcg gcaccggcaa cggcacgcgg ctgcagctct actcctgctg gggcggcaac   1320
aaccagaagt ggtcctacaa cgcctaa                                       1347
```

<210> SEQ ID NO 8
<211> LENGTH: 972
<212> TYPE: DNA
<213> ORGANISM: Nonomuraea flexuosa
<220> FEATURE:
<223> OTHER INFORMATION: Sequence encoding the AM50 core and linker
      regions, includes a STOP codon

<400> SEQUENCE: 8

```
gcggcgagca cgctcgccga gggtgccgcg cagcacaacc ggtacttcgg cgtggccatc     60
gccgcgaaca ggctcaacga ctcggtctac accaacatcg cgaaccgcga gttcaactcg    120
gtgacggccg agaacgagat gaagatcgac gccaccgagc cgcagcaggg gcggttcgac    180
ttcacccagg ccgaccggat ctacaactgg gcgcgccaga acggcaagca ggtccgcggc    240
cacaccctgg cctggcactc gcagcagccg cagtggatgc agaacctcag cggccaggcg    300
ctgcgccagg cgatgatcaa ccacatccag ggggtcatgt cctactaccg gggcaagatc    360
ccgatctggg acgtggtgaa cgaggcgttc gaggacggca actccggccg ccggcgcgac    420
tccaacctcc agcgcaccgg taacgactgg atcgaggtcg cgttccgcac cgcccgccag    480
gcggacccct cggccaagct ctgctacaac gactacaaca tcgagaactg aacgcggcc     540 aagacccagg cggtctacaa catggtgcgg gacttcaagt cccgcggcgt gcccatcgac    600
tgcgtgggct ccagtcgca cttcaacagc ggtaacccgt acaacccgaa cttccgcacc    660
accctgcagc agttcgcggc cctcggcgtg gacgtcgagg tcaccgagct ggacatcgag    720
aacgccccgg cccagaccta cgccagcgtg atccgggact gcctggccgt ggaccgctgc    780
accggcatca ccgtctgggg tgtccgcgac agcgactcct ggcgctcgta ccagaacccg    840
ctgctgttcg acaacaacgg caacaagaag caggcctact acgcggtgct cgacgccctg    900
aacgagggct ccgacgacgg tggcggcccg tccaacccgc cggtctcgcc gccgcgggt    960 ggcggttcct aa                                                       972
```

<210> SEQ ID NO 9
<211> LENGTH: 906
<212> TYPE: DNA
<213> ORGANISM: Nonomuraea flexuosa
<220> FEATURE:
<223> OTHER INFORMATION: Sequence encoding the AM50 core region, includes a STOP codon

<400> SEQUENCE: 9

```
gcggcgagca cgctcgccga gggtgccgcg cagcacaacc ggtacttcgg cgtggccatc      60
gccgcgaaca ggctcaacga ctcggtctac accaacatcg cgaaccgcga gttcaactcg     120
gtgacggccg agaacgagat gaagatcgac gccaccgagc cgcagcaggg gcggttcgac     180
ttcacccagg ccgaccggat ctacaactgg gcgcgccaga acggcaagca ggtccgcggc     240
cacaccctgg cctggcactc gcagcagccg cagtggatgc agaacctcag cggccaggcg     300
ctgcgccagg cgatgatcaa ccacatccag ggggtcatgt cctactaccg ggcaagatc     360
ccgatctggg acgtggtgaa cgaggcgttc gaggacggca actccggccg ccggcgcgac     420
tccaacctcc agcgcaccgg taacgactgg atcgaggtcg cgttccgcac cgcccgccag     480
gcggacccct cggccaagct ctgctacaac gactacaaca tcgagaactg aacgcggcc     540
aagacccagg cggtctacaa catggtgcgg gacttcaagt cccgcggcgt gcccatcgac     600
tgcgtgggct tccagtcgca cttcaacagc ggtaacccgt acaacccgaa cttccgcacc     660
accctgcagc agttcgcggc cctcggcgtg acgtcgagg tcaccgagct ggacatcgag     720
aacgccccgg cccagaccta cgccagcgtg atccgggact gcctggccgt ggaccgctgc     780
accggcatca ccgtctgggg tgtccgcgac agcgactcct ggcgctcgta ccagaacccg     840
ctgctgttcg acaacaacgg caacaagaag caggcctact acgcggtgct cgacgccctg     900
aactaa                                                                906
```

<210> SEQ ID NO 10
<211> LENGTH: 344
<212> TYPE: PRT
<213> ORGANISM: Nonomuraea flexuosa
<220> FEATURE:
<223> OTHER INFORMATION: Nf Xyn11A amino acid sequence (AJ508952) encoded by the Nf xyn11A gene

<400> SEQUENCE: 10

```
Met Asn Glu Pro Leu Thr Ile Thr Gln Ala Arg Arg Arg Arg Arg Leu
1               5                   10                  15

Gly Leu Arg Arg Ile Val Thr Ser Ala Phe Ala Leu Ala Leu Ala Ile
            20                  25                  30

Ala Gly Ala Leu Leu Pro Gly Thr Ala His Ala Asp Thr Thr Ile Thr
        35                  40                  45

Gln Asn Gln Thr Gly Tyr Asp Asn Gly Tyr Phe Tyr Ser Phe Trp Thr
    50                  55                  60

Asp Ala Pro Gly Thr Val Ser Met Thr Leu His Ser Gly Gly Ser Tyr
65                  70                  75                  80

Ser Thr Ser Trp Arg Asn Thr Gly Asn Phe Val Ala Gly Lys Gly Trp
                85                  90                  95

Ser Thr Gly Gly Arg Arg Thr Val Thr Tyr Asn Ala Ser Phe Asn Pro
            100                 105                 110

Ser Gly Asn Ala Tyr Leu Thr Leu Tyr Gly Trp Thr Arg Asn Pro Leu
        115                 120                 125
```

```
Val Glu Tyr Tyr Ile Val Glu Ser Trp Gly Thr Tyr Arg Pro Thr Gly
            130                 135                 140

Thr Tyr Lys Gly Thr Val Thr Thr Asp Gly Gly Thr Tyr Asp Ile Tyr
145                 150                 155                 160

Glu Thr Trp Arg Tyr Asn Ala Pro Ser Ile Glu Gly Thr Arg Thr Phe
                165                 170                 175

Gln Gln Phe Trp Ser Val Arg Gln Gln Lys Arg Thr Ser Gly Thr Ile
            180                 185                 190

Thr Ile Gly Asn His Phe Asp Ala Trp Ala Arg Ala Gly Met Asn Leu
        195                 200                 205

Gly Ser His Asp Tyr Gln Ile Met Ala Thr Glu Gly Tyr Gln Ser Ser
    210                 215                 220

Gly Ser Ser Thr Val Ser Ile Ser Glu Gly Gly Asn Pro Gly Asn Pro
225                 230                 235                 240

Gly Asn Pro Gly Asn Pro Gly Asn Pro Gly Asn Pro Gly Asn Pro Gly
                245                 250                 255

Gly Gly Cys Val Ala Thr Leu Ser Ala Gly Gln Gln Trp Ser Asp Arg
            260                 265                 270

Tyr Asn Leu Asn Val Ser Val Ser Gly Ser Asn Asn Trp Thr Val Arg
            275                 280                 285

Met Asp Val Pro Tyr Pro Ala Arg Ile Ile Ala Thr Trp Asn Ile His
    290                 295                 300

Ala Gln Trp Pro Glu Ser Gln Val Leu Ile Ala Arg Pro Asn Gly Asn
305                 310                 315                 320

Gly Asn Asn Trp Gly Val Thr Ile Gln His Asn Gly Asn Trp Thr Trp
                325                 330                 335

Pro Thr Val Thr Cys Thr Ala Asn
            340

<210> SEQ ID NO 11
<211> LENGTH: 301
<212> TYPE: PRT
<213> ORGANISM: Nonomuraea flexuosa
<220> FEATURE:
<223> OTHER INFORMATION: r33.4 kDa = AM35 = full length mature Nf Xyn11A
      protein, encoded by am35 and am35* genes

<400> SEQUENCE: 11

Asp Thr Thr Ile Thr Gln Asn Gln Thr Gly Tyr Asp Asn Gly Tyr Phe
1               5                   10                  15

Tyr Ser Phe Trp Thr Asp Ala Pro Gly Thr Val Ser Met Thr Leu His
            20                  25                  30

Ser Gly Gly Ser Tyr Ser Thr Ser Trp Arg Asn Thr Gly Asn Phe Val
        35                  40                  45

Ala Gly Lys Gly Trp Ser Thr Gly Gly Arg Arg Thr Val Thr Tyr Asn
    50                  55                  60

Ala Ser Phe Asn Pro Ser Gly Asn Ala Tyr Leu Thr Leu Tyr Gly Trp
65                  70                  75                  80

Thr Arg Asn Pro Leu Val Glu Tyr Tyr Ile Val Glu Ser Trp Gly Thr
                85                  90                  95

Tyr Arg Pro Thr Gly Thr Tyr Lys Gly Thr Val Thr Thr Asp Gly Gly
            100                 105                 110

Thr Tyr Asp Ile Tyr Glu Thr Trp Arg Tyr Asn Ala Pro Ser Ile Glu
        115                 120                 125

Gly Thr Arg Thr Phe Gln Gln Phe Trp Ser Val Arg Gln Gln Lys Arg
    130                 135                 140
```

```
Thr Ser Gly Thr Ile Thr Ile Gly Asn His Phe Asp Ala Trp Ala Arg
145                 150                 155                 160

Ala Gly Met Asn Leu Gly Ser His Asp Tyr Gln Ile Met Ala Thr Glu
            165                 170                 175

Gly Tyr Gln Ser Ser Gly Ser Ser Thr Val Ser Ile Ser Glu Gly Gly
        180                 185                 190

Asn Pro Gly Asn Pro Gly Asn Pro Gly Asn Pro Gly Asn Pro Gly Asn
            195                 200                 205

Pro Gly Asn Pro Gly Gly Cys Val Ala Thr Leu Ser Ala Gly Gln
    210                 215                 220

Gln Trp Ser Asp Arg Tyr Asn Leu Asn Val Ser Val Ser Gly Ser Asn
225                 230                 235                 240

Asn Trp Thr Val Arg Met Asp Val Pro Tyr Pro Ala Arg Ile Ile Ala
                245                 250                 255

Thr Trp Asn Ile His Ala Gln Trp Pro Glu Ser Gln Val Leu Ile Ala
            260                 265                 270

Arg Pro Asn Gly Asn Gly Asn Trp Gly Val Thr Ile Gln His Asn
        275                 280                 285

Gly Asn Trp Thr Trp Pro Thr Val Thr Cys Thr Ala Asn
    290                 295                 300

<210> SEQ ID NO 12
<211> LENGTH: 220
<212> TYPE: PRT
<213> ORGANISM: Nonomuraea flexuosa
<220> FEATURE:
<223> OTHER INFORMATION: AM24, truncated form from AM35, encoded by am24
      and am24* genes

<400> SEQUENCE: 12

Asp Thr Thr Ile Thr Gln Asn Gln Thr Gly Tyr Asp Asn Gly Tyr Phe
1               5                   10                  15

Tyr Ser Phe Trp Thr Asp Ala Pro Gly Thr Val Ser Met Thr Leu His
            20                  25                  30

Ser Gly Gly Ser Tyr Ser Thr Ser Trp Arg Asn Thr Gly Asn Phe Val
        35                  40                  45

Ala Gly Lys Gly Trp Ser Thr Gly Gly Arg Arg Thr Val Thr Tyr Asn
50                  55                  60

Ala Ser Phe Asn Pro Ser Gly Asn Ala Tyr Leu Thr Leu Tyr Gly Trp
65                  70                  75                  80

Thr Arg Asn Pro Leu Val Glu Tyr Tyr Ile Val Glu Ser Trp Gly Thr
                85                  90                  95

Tyr Arg Pro Thr Gly Thr Tyr Lys Gly Thr Val Thr Thr Asp Gly Gly
            100                 105                 110

Thr Tyr Asp Ile Tyr Glu Thr Trp Arg Tyr Asn Ala Pro Ser Ile Glu
        115                 120                 125

Gly Thr Arg Thr Phe Gln Gln Phe Trp Ser Val Arg Gln Gln Lys Arg
130                 135                 140

Thr Ser Gly Thr Ile Thr Ile Gly Asn His Phe Asp Ala Trp Ala Arg
145                 150                 155                 160

Ala Gly Met Asn Leu Gly Ser His Asp Tyr Gln Ile Met Ala Thr Glu
            165                 170                 175

Gly Tyr Gln Ser Ser Gly Ser Ser Thr Val Ser Ile Ser Glu Gly Gly
        180                 185                 190

Asn Pro Gly Asn Pro Gly Asn Pro Gly Asn Pro Gly Asn Pro Gly Asn
```

```
                195                 200                 205
Pro Gly Asn Pro Gly Gly Gly Cys Val Ala Thr Leu
    210                 215                 220

<210> SEQ ID NO 13
<211> LENGTH: 217
<212> TYPE: PRT
<213> ORGANISM: Nonomuraea flexuosa
<220> FEATURE:
<223> OTHER INFORMATION: r23.8 kDa, truncated form from AM35

<400> SEQUENCE: 13

Asp Thr Thr Ile Thr Gln Asn Gln Thr Gly Tyr Asp Asn Gly Tyr Phe
1               5                   10                  15

Tyr Ser Phe Trp Thr Asp Ala Pro Gly Thr Val Ser Met Thr Leu His
            20                  25                  30

Ser Gly Gly Ser Tyr Ser Thr Ser Trp Arg Asn Thr Gly Asn Phe Val
        35                  40                  45

Ala Gly Lys Gly Trp Ser Thr Gly Gly Arg Arg Thr Val Thr Tyr Asn
    50                  55                  60

Ala Ser Phe Asn Pro Ser Gly Asn Ala Tyr Leu Thr Leu Tyr Gly Trp
65                  70                  75                  80

Thr Arg Asn Pro Leu Val Glu Tyr Tyr Ile Val Glu Ser Trp Gly Thr
                85                  90                  95

Tyr Arg Pro Thr Gly Thr Tyr Lys Gly Thr Val Thr Thr Asp Gly Gly
            100                 105                 110

Thr Tyr Asp Ile Tyr Glu Thr Trp Arg Tyr Asn Ala Pro Ser Ile Glu
        115                 120                 125

Gly Thr Arg Thr Phe Gln Gln Phe Trp Ser Val Arg Gln Gln Lys Arg
    130                 135                 140

Thr Ser Gly Thr Ile Thr Ile Gly Asn His Phe Asp Ala Trp Ala Arg
145                 150                 155                 160

Ala Gly Met Asn Leu Gly Ser His Asp Tyr Gln Ile Met Ala Thr Glu
                165                 170                 175

Gly Tyr Gln Ser Ser Gly Ser Ser Thr Val Ser Ile Ser Glu Gly Gly
            180                 185                 190

Asn Pro Gly Asn Pro Gly Asn Pro Gly Asn Pro Gly Asn Pro Gly Asn
        195                 200                 205

Pro Gly Asn Pro Gly Gly Gly Cys Val
    210                 215

<210> SEQ ID NO 14
<211> LENGTH: 193
<212> TYPE: PRT
<213> ORGANISM: Nonomuraea flexuosa
<220> FEATURE:
<223> OTHER INFORMATION: r22.0 kDa, truncated form from AM35

<400> SEQUENCE: 14

Asp Thr Thr Ile Thr Gln Asn Gln Thr Gly Tyr Asp Asn Gly Tyr Phe
1               5                   10                  15

Tyr Ser Phe Trp Thr Asp Ala Pro Gly Thr Val Ser Met Thr Leu His
            20                  25                  30

Ser Gly Gly Ser Tyr Ser Thr Ser Trp Arg Asn Thr Gly Asn Phe Val
        35                  40                  45

Ala Gly Lys Gly Trp Ser Thr Gly Gly Arg Arg Thr Val Thr Tyr Asn
    50                  55                  60
```

```
Ala Ser Phe Asn Pro Ser Gly Asn Ala Tyr Leu Thr Leu Tyr Gly Trp
 65                  70                  75                  80

Thr Arg Asn Pro Leu Val Glu Tyr Tyr Ile Val Glu Ser Trp Gly Thr
                 85                  90                  95

Tyr Arg Pro Thr Gly Thr Tyr Lys Gly Thr Val Thr Asp Gly Gly
            100                 105                 110

Thr Tyr Asp Ile Tyr Glu Thr Trp Arg Tyr Asn Ala Pro Ser Ile Glu
            115                 120                 125

Gly Thr Arg Thr Phe Gln Gln Phe Trp Ser Val Arg Gln Gln Lys Arg
130                 135                 140

Thr Ser Gly Thr Ile Thr Ile Gly Asn His Phe Asp Ala Trp Ala Arg
145                 150                 155                 160

Ala Gly Met Asn Leu Gly Ser His Asp Tyr Gln Ile Met Ala Thr Glu
                165                 170                 175

Gly Tyr Gln Ser Ser Gly Ser Ser Thr Val Ser Ile Ser Glu Gly Gly
            180                 185                 190

Asn
```

```
<210> SEQ ID NO 15
<211> LENGTH: 492
<212> TYPE: PRT
<213> ORGANISM: Nonomuraea flexuosa
<220> FEATURE:
<223> OTHER INFORMATION: Nf Xyn10A, the amino acid sequence (AJ508953)
      encoded by the Nfxyn10A gene

<400> SEQUENCE: 15
```

```
Met Gly Val Asn Ala Phe Pro Arg Pro Gly Ala Arg Arg Phe Thr Gly
  1               5                  10                  15

Gly Leu Tyr Arg Ala Leu Ala Ala Ala Thr Val Ser Val Val Gly Val
                 20                  25                  30

Val Thr Ala Leu Thr Val Thr Gln Pro Ala Ser Ala Ala Ala Ser Thr
             35                  40                  45

Leu Ala Glu Gly Ala Ala Gln His Asn Arg Tyr Phe Gly Val Ala Ile
 50                  55                  60

Ala Ala Asn Arg Leu Asn Asp Ser Val Tyr Thr Asn Ile Ala Asn Arg
 65                  70                  75                  80

Glu Phe Asn Ser Val Thr Ala Glu Asn Glu Met Lys Ile Asp Ala Thr
                 85                  90                  95

Glu Pro Gln Gln Gly Arg Phe Asp Phe Thr Gln Ala Asp Arg Ile Tyr
            100                 105                 110

Asn Trp Ala Arg Gln Asn Gly Lys Gln Val Arg Gly His Thr Leu Ala
            115                 120                 125

Trp His Ser Gln Gln Pro Gln Trp Met Gln Asn Leu Ser Gly Gln Ala
130                 135                 140

Leu Arg Gln Ala Met Ile Asn His Ile Gln Gly Val Met Ser Tyr Tyr
145                 150                 155                 160

Arg Gly Lys Ile Pro Ile Trp Asp Val Val Asn Glu Ala Phe Glu Asp
                165                 170                 175

Gly Asn Ser Gly Arg Arg Asp Ser Asn Leu Gln Arg Thr Gly Asn
            180                 185                 190

Asp Trp Ile Glu Val Ala Phe Arg Thr Ala Arg Gln Ala Asp Pro Ser
            195                 200                 205

Ala Lys Leu Cys Tyr Asn Asp Tyr Asn Ile Glu Asn Trp Asn Ala Ala
    210                 215                 220
```

```
Lys Thr Gln Ala Val Tyr Asn Met Val Arg Asp Phe Lys Ser Arg Gly
225                 230                 235                 240

Val Pro Ile Asp Cys Val Gly Phe Gln Ser His Phe Asn Ser Gly Asn
                245                 250                 255

Pro Tyr Asn Pro Asn Phe Arg Thr Thr Leu Gln Gln Phe Ala Ala Leu
            260                 265                 270

Gly Val Asp Val Glu Val Thr Glu Leu Asp Ile Glu Asn Ala Pro Ala
        275                 280                 285

Gln Thr Tyr Ala Ser Val Ile Arg Asp Cys Leu Ala Val Asp Arg Cys
    290                 295                 300

Thr Gly Ile Thr Val Trp Gly Val Arg Asp Ser Asp Ser Trp Arg Ser
305                 310                 315                 320

Tyr Gln Asn Pro Leu Leu Phe Asp Asn Gly Asn Lys Lys Gln Ala
                325                 330                 335

Tyr Tyr Ala Val Leu Asp Ala Leu Asn Glu Gly Ser Asp Asp Gly Gly
            340                 345                 350

Gly Pro Ser Asn Pro Pro Val Ser Pro Pro Gly Gly Gly Ser Gly
        355                 360                 365

Gln Ile Arg Gly Val Ala Ser Asn Arg Cys Ile Asp Val Pro Asn Gly
370                 375                 380

Asn Thr Ala Asp Gly Thr Gln Val Gln Leu Tyr Asp Cys His Ser Gly
385                 390                 395                 400

Ser Asn Gln Gln Trp Thr Tyr Thr Ser Ser Gly Glu Phe Arg Ile Phe
                405                 410                 415

Gly Asn Lys Cys Leu Asp Ala Gly Gly Ser Ser Asn Gly Ala Val Val
            420                 425                 430

Gln Ile Tyr Ser Cys Trp Gly Gly Ala Asn Gln Lys Trp Glu Leu Arg
        435                 440                 445

Ala Asp Gly Thr Ile Val Gly Val Gln Ser Gly Leu Cys Leu Asp Ala
    450                 455                 460

Val Gly Gly Gly Thr Gly Asn Gly Thr Arg Leu Gln Leu Tyr Ser Cys
465                 470                 475                 480

Trp Gly Gly Asn Asn Gln Lys Trp Ser Tyr Asn Ala
                485                 490

<210> SEQ ID NO 16
<211> LENGTH: 448
<212> TYPE: PRT
<213> ORGANISM: Nonomuraea flexuosa
<220> FEATURE:
<223> OTHER INFORMATION: AM50, full length mature Nf Xyn10A

<400> SEQUENCE: 16

Ala Ala Ser Thr Leu Ala Glu Gly Ala Ala Gln His Asn Arg Tyr Phe
1               5                   10                  15

Gly Val Ala Ile Ala Ala Asn Arg Leu Asn Asp Ser Val Tyr Thr Asn
                20                  25                  30

Ile Ala Asn Arg Glu Phe Asn Ser Val Thr Ala Glu Asn Glu Met Lys
            35                  40                  45

Ile Asp Ala Thr Glu Pro Gln Gln Gly Arg Phe Asp Phe Thr Gln Ala
    50                  55                  60

Asp Arg Ile Tyr Asn Trp Ala Arg Gln Asn Gly Lys Gln Val Arg Gly
65                  70                  75                  80

His Thr Leu Ala Trp His Ser Gln Gln Pro Gln Trp Met Gln Asn Leu
                85                  90                  95
```

Ser Gly Gln Ala Leu Arg Gln Ala Met Ile Asn His Ile Gln Gly Val
                100                 105                 110

Met Ser Tyr Tyr Arg Gly Lys Ile Pro Ile Trp Asp Val Val Asn Glu
            115                 120                 125

Ala Phe Glu Asp Gly Asn Ser Gly Arg Arg Asp Ser Asn Leu Gln
        130                 135                 140

Arg Thr Gly Asn Asp Trp Ile Glu Val Ala Phe Arg Thr Ala Arg Gln
145                 150                 155                 160

Ala Asp Pro Ser Ala Lys Leu Cys Tyr Asn Asp Tyr Asn Ile Glu Asn
                165                 170                 175

Trp Asn Ala Ala Lys Thr Gln Ala Val Tyr Asn Met Val Arg Asp Phe
            180                 185                 190

Lys Ser Arg Gly Val Pro Ile Asp Cys Val Gly Phe Gln Ser His Phe
        195                 200                 205

Asn Ser Gly Asn Pro Tyr Asn Pro Asn Phe Arg Thr Thr Leu Gln Gln
    210                 215                 220

Phe Ala Ala Leu Gly Val Asp Val Glu Val Thr Glu Leu Asp Ile Glu
225                 230                 235                 240

Asn Ala Pro Ala Gln Thr Tyr Ala Ser Val Ile Arg Asp Cys Leu Ala
                245                 250                 255

Val Asp Arg Cys Thr Gly Ile Thr Val Trp Gly Val Arg Asp Ser Asp
            260                 265                 270

Ser Trp Arg Ser Tyr Gln Asn Pro Leu Leu Phe Asp Asn Asn Gly Asn
        275                 280                 285

Lys Lys Gln Ala Tyr Tyr Ala Val Leu Asp Ala Leu Asn Glu Gly Ser
    290                 295                 300

Asp Asp Gly Gly Gly Pro Ser Asn Pro Val Ser Pro Pro Gly
305                 310                 315                 320

Gly Gly Ser Gly Gln Ile Arg Gly Val Ala Ser Asn Arg Cys Ile Asp
                325                 330                 335

Val Pro Asn Gly Asn Thr Ala Asp Gly Thr Gln Val Gln Leu Tyr Asp
            340                 345                 350

Cys His Ser Gly Ser Asn Gln Gln Trp Thr Tyr Thr Ser Ser Gly Glu
        355                 360                 365

Phe Arg Ile Phe Gly Asn Lys Cys Leu Asp Ala Gly Gly Ser Ser Asn
    370                 375                 380

Gly Ala Val Val Gln Ile Tyr Ser Cys Trp Gly Gly Ala Asn Gln Lys
385                 390                 395                 400

Trp Glu Leu Arg Ala Asp Gly Thr Ile Val Gly Val Gln Ser Gly Leu
                405                 410                 415

Cys Leu Asp Ala Val Gly Gly Thr Gly Asn Gly Thr Arg Leu Gln
            420                 425                 430

Leu Tyr Ser Cys Trp Gly Gly Asn Asn Gln Lys Trp Ser Tyr Asn Ala
        435                 440                 445

<210> SEQ ID NO 17
<211> LENGTH: 323
<212> TYPE: PRT
<213> ORGANISM: Nonomuraea flexuosa
<220> FEATURE:
<223> OTHER INFORMATION: AM50 core and linker, truncated form from AM50

<400> SEQUENCE: 17

Ala Ala Ser Thr Leu Ala Glu Gly Ala Ala Gln His Asn Arg Tyr Phe
1               5                   10                  15

```
Gly Val Ala Ile Ala Ala Asn Arg Leu Asn Asp Ser Val Tyr Thr Asn
             20                  25                  30

Ile Ala Asn Arg Glu Phe Asn Ser Val Thr Ala Glu Asn Glu Met Lys
             35                  40                  45

Ile Asp Ala Thr Glu Pro Gln Gln Gly Arg Phe Asp Phe Thr Gln Ala
             50                  55                  60

Asp Arg Ile Tyr Asn Trp Ala Arg Gln Asn Gly Lys Gln Val Arg Gly
 65                  70                  75                  80

His Thr Leu Ala Trp His Ser Gln Pro Gln Trp Met Gln Asn Leu
             85                  90                  95

Ser Gly Gln Ala Leu Arg Gln Ala Met Ile Asn His Ile Gln Gly Val
            100                 105                 110

Met Ser Tyr Tyr Arg Gly Lys Ile Pro Ile Trp Asp Val Val Asn Glu
            115                 120                 125

Ala Phe Glu Asp Gly Asn Ser Gly Arg Arg Arg Asp Ser Asn Leu Gln
        130                 135                 140

Arg Thr Gly Asn Asp Trp Ile Glu Val Ala Phe Arg Thr Ala Arg Gln
145                 150                 155                 160

Ala Asp Pro Ser Ala Lys Leu Cys Tyr Asn Asp Tyr Asn Ile Glu Asn
                165                 170                 175

Trp Asn Ala Ala Lys Thr Gln Ala Val Tyr Asn Met Val Arg Asp Phe
            180                 185                 190

Lys Ser Arg Gly Val Pro Ile Asp Cys Val Gly Phe Gln Ser His Phe
        195                 200                 205

Asn Ser Gly Asn Pro Tyr Asn Pro Asn Phe Arg Thr Thr Leu Gln Gln
    210                 215                 220

Phe Ala Ala Leu Gly Val Asp Val Glu Val Thr Glu Leu Asp Ile Glu
225                 230                 235                 240

Asn Ala Pro Ala Gln Thr Tyr Ala Ser Val Ile Arg Asp Cys Leu Ala
                245                 250                 255

Val Asp Arg Cys Thr Gly Ile Thr Val Trp Gly Val Arg Asp Ser Asp
            260                 265                 270

Ser Trp Arg Ser Tyr Gln Asn Pro Leu Leu Phe Asp Asn Asn Gly Asn
        275                 280                 285

Lys Lys Gln Ala Tyr Tyr Ala Val Leu Asp Ala Leu Asn Glu Gly Ser
    290                 295                 300

Asp Asp Gly Gly Gly Pro Ser Asn Pro Pro Val Ser Pro Pro Pro Gly
305                 310                 315                 320

Gly Gly Ser

<210> SEQ ID NO 18
<211> LENGTH: 301
<212> TYPE: PRT
<213> ORGANISM: Nonomuraea flexuosa
<220> FEATURE:
<223> OTHER INFORMATION: AM50 core, truncated form from AM50

<400> SEQUENCE: 18

Ala Ala Ser Thr Leu Ala Glu Gly Ala Ala Gln His Asn Arg Tyr Phe
 1               5                  10                  15

Gly Val Ala Ile Ala Ala Asn Arg Leu Asn Asp Ser Val Tyr Thr Asn
             20                  25                  30

Ile Ala Asn Arg Glu Phe Asn Ser Val Thr Ala Glu Asn Glu Met Lys
             35                  40                  45

Ile Asp Ala Thr Glu Pro Gln Gln Gly Arg Phe Asp Phe Thr Gln Ala
```

```
                50                  55                  60
Asp Arg Ile Tyr Asn Trp Ala Arg Gln Asn Gly Lys Gln Val Arg Gly
 65                  70                  75                  80

His Thr Leu Ala Trp His Ser Gln Gln Pro Gln Trp Met Gln Asn Leu
                 85                  90                  95

Ser Gly Gln Ala Leu Arg Gln Ala Met Ile Asn His Ile Gln Gly Val
                100                 105                 110

Met Ser Tyr Tyr Arg Gly Lys Ile Pro Ile Trp Asp Val Val Asn Glu
                115                 120                 125

Ala Phe Glu Asp Gly Asn Ser Gly Arg Arg Asp Ser Asn Leu Gln
130                 135                 140

Arg Thr Gly Asn Asp Trp Ile Glu Val Ala Phe Arg Thr Ala Arg Gln
145                 150                 155                 160

Ala Asp Pro Ser Ala Lys Leu Cys Tyr Asn Asp Tyr Asn Ile Glu Asn
                165                 170                 175

Trp Asn Ala Ala Lys Thr Gln Ala Val Tyr Asn Met Val Arg Asp Phe
                180                 185                 190

Lys Ser Arg Gly Val Pro Ile Asp Cys Val Gly Phe Gln Ser His Phe
                195                 200                 205

Asn Ser Gly Asn Pro Tyr Asn Pro Asn Phe Arg Thr Thr Leu Gln Gln
                210                 215                 220

Phe Ala Ala Leu Gly Val Asp Val Glu Val Thr Glu Leu Asp Ile Glu
225                 230                 235                 240

Asn Ala Pro Ala Gln Thr Tyr Ala Ser Val Ile Arg Asp Cys Leu Ala
                245                 250                 255

Val Asp Arg Cys Thr Gly Ile Thr Val Trp Gly Val Arg Asp Ser Asp
                260                 265                 270

Ser Trp Arg Ser Tyr Gln Asn Pro Leu Leu Phe Asp Asn Asn Gly Asn
                275                 280                 285

Lys Lys Gln Ala Tyr Tyr Ala Val Leu Asp Ala Leu Asn
                290                 295                 300

<210> SEQ ID NO 19
<211> LENGTH: 406
<212> TYPE: PRT
<213> ORGANISM: Nonomuraea flexuosa
<220> FEATURE:
<223> OTHER INFORMATION: AM50 core + linker + alpha/beta domains of the
      tail

<400> SEQUENCE: 19

Ala Ala Ser Thr Leu Ala Glu Gly Ala Ala Gln His Asn Arg Tyr Phe
 1               5                  10                  15

Gly Val Ala Ile Ala Ala Asn Arg Leu Asn Asp Ser Val Tyr Thr Asn
                20                  25                  30

Ile Ala Asn Arg Glu Phe Asn Ser Val Thr Ala Glu Asn Glu Met Lys
            35                  40                  45

Ile Asp Ala Thr Glu Pro Gln Gln Gly Arg Phe Asp Phe Thr Gln Ala
 50                  55                  60

Asp Arg Ile Tyr Asn Trp Ala Arg Gln Asn Gly Lys Gln Val Arg Gly
 65                  70                  75                  80

His Thr Leu Ala Trp His Ser Gln Gln Pro Gln Trp Met Gln Asn Leu
                 85                  90                  95

Ser Gly Gln Ala Leu Arg Gln Ala Met Ile Asn His Ile Gln Gly Val
                100                 105                 110
```

```
Met Ser Tyr Tyr Arg Gly Lys Ile Pro Ile Trp Asp Val Val Asn Glu
        115                 120                 125

Ala Phe Glu Asp Gly Asn Ser Gly Arg Arg Arg Asp Ser Asn Leu Gln
        130                 135                 140

Arg Thr Gly Asn Asp Trp Ile Glu Val Ala Phe Arg Thr Ala Arg Gln
145                 150                 155                 160

Ala Asp Pro Ser Ala Lys Leu Cys Tyr Asn Asp Tyr Asn Ile Glu Asn
                165                 170                 175

Trp Asn Ala Ala Lys Thr Gln Ala Val Tyr Asn Met Val Arg Asp Phe
                180                 185                 190

Lys Ser Arg Gly Val Pro Ile Asp Cys Val Gly Phe Gln Ser His Phe
                195                 200                 205

Asn Ser Gly Asn Pro Tyr Asn Pro Asn Phe Arg Thr Thr Leu Gln Gln
        210                 215                 220

Phe Ala Ala Leu Gly Val Asp Val Glu Val Thr Glu Leu Asp Ile Glu
225                 230                 235                 240

Asn Ala Pro Ala Gln Thr Tyr Ala Ser Val Ile Arg Asp Cys Leu Ala
                245                 250                 255

Val Asp Arg Cys Thr Gly Ile Thr Val Trp Gly Val Arg Asp Ser Asp
                260                 265                 270

Ser Trp Arg Ser Tyr Gln Asn Pro Leu Leu Phe Asp Asn Asn Gly Asn
        275                 280                 285

Lys Lys Gln Ala Tyr Tyr Ala Val Leu Asp Ala Leu Asn Glu Gly Ser
        290                 295                 300

Asp Asp Gly Gly Gly Pro Ser Asn Pro Pro Val Ser Pro Pro Pro Gly
305                 310                 315                 320

Gly Gly Ser Gly Gln Ile Arg Gly Val Ala Ser Asn Arg Cys Ile Asp
                325                 330                 335

Val Pro Asn Gly Asn Thr Ala Asp Gly Thr Gln Val Gln Leu Tyr Asp
                340                 345                 350

Cys His Ser Gly Ser Asn Gln Gln Trp Thr Tyr Thr Ser Ser Gly Glu
        355                 360                 365

Phe Arg Ile Phe Gly Asn Lys Cys Leu Asp Ala Gly Gly Ser Ser Asn
        370                 375                 380

Gly Ala Val Val Gln Ile Tyr Ser Cys Trp Gly Gly Ala Asn Gln Lys
385                 390                 395                 400

Trp Glu Leu Arg Ala Asp
                405

<210> SEQ ID NO 20
<211> LENGTH: 366
<212> TYPE: PRT
<213> ORGANISM: Nonomuraea flexuosa
<220> FEATURE:
<223> OTHER INFORMATION: AM50 core + linker + alpha domain of the tail

<400> SEQUENCE: 20

Ala Ala Ser Thr Leu Ala Glu Gly Ala Ala Gln His Asn Arg Tyr Phe
1               5                   10                  15

Gly Val Ala Ile Ala Ala Asn Arg Leu Asn Asp Ser Val Tyr Thr Asn
                20                  25                  30

Ile Ala Asn Arg Glu Phe Asn Ser Val Thr Ala Glu Asn Glu Met Lys
            35                  40                  45

Ile Asp Ala Thr Glu Pro Gln Gln Gly Arg Phe Asp Phe Thr Gln Ala
        50                  55                  60
```

```
Asp Arg Ile Tyr Asn Trp Ala Arg Gln Asn Gly Lys Gln Val Arg Gly
 65                  70                  75                  80

His Thr Leu Ala Trp His Ser Gln Gln Pro Gln Trp Met Gln Asn Leu
                 85                  90                  95

Ser Gly Gln Ala Leu Arg Gln Ala Met Ile Asn His Ile Gln Gly Val
            100                 105                 110

Met Ser Tyr Tyr Arg Gly Lys Ile Pro Ile Trp Asp Val Val Asn Glu
            115                 120                 125

Ala Phe Glu Asp Gly Asn Ser Gly Arg Arg Arg Asp Ser Asn Leu Gln
        130                 135                 140

Arg Thr Gly Asn Asp Trp Ile Glu Val Ala Phe Arg Thr Ala Arg Gln
145                 150                 155                 160

Ala Asp Pro Ser Ala Lys Leu Cys Tyr Asn Asp Tyr Asn Ile Glu Asn
                165                 170                 175

Trp Asn Ala Ala Lys Thr Gln Ala Val Tyr Asn Met Val Arg Asp Phe
            180                 185                 190

Lys Ser Arg Gly Val Pro Ile Asp Cys Val Gly Phe Gln Ser His Phe
        195                 200                 205

Asn Ser Gly Asn Pro Tyr Asn Pro Asn Phe Arg Thr Thr Leu Gln Gln
    210                 215                 220

Phe Ala Ala Leu Gly Val Asp Val Glu Val Thr Glu Leu Asp Ile Glu
225                 230                 235                 240

Asn Ala Pro Ala Gln Thr Tyr Ala Ser Val Ile Arg Asp Cys Leu Ala
                245                 250                 255

Val Asp Arg Cys Thr Gly Ile Thr Val Trp Gly Val Arg Asp Ser Asp
            260                 265                 270

Ser Trp Arg Ser Tyr Gln Asn Pro Leu Leu Phe Asp Asn Asn Gly Asn
        275                 280                 285

Lys Lys Gln Ala Tyr Tyr Ala Val Leu Asp Ala Leu Asn Glu Gly Ser
    290                 295                 300

Asp Asp Gly Gly Gly Pro Ser Asn Pro Pro Val Ser Pro Pro Pro Gly
305                 310                 315                 320

Gly Gly Ser Gly Gln Ile Arg Gly Val Ala Ser Asn Arg Cys Ile Asp
            325                 330                 335

Val Pro Asn Gly Asn Thr Ala Asp Gly Thr Gln Val Gln Leu Tyr Asp
            340                 345                 350

Cys His Ser Gly Ser Asn Gln Gln Trp Thr Tyr Thr Ser Ser
        355                 360                 365

<210> SEQ ID NO 21
<211> LENGTH: 4
<212> TYPE: PRT
<213> ORGANISM: Nonomuraea flexuosa
<220> FEATURE:
<223> OTHER INFORMATION: A synthetic linker sequence coding for a
      Kex2-like protease cleavage signal Lys-Arg included in all the
      constructs to ensure cleavage of the fusion protein.

<400> SEQUENCE: 21

Arg Asp Lys Arg
1

<210> SEQ ID NO 22
<211> LENGTH: 5
<212> TYPE: PRT
<213> ORGANISM: Nonomuraea flexuosa
<220> FEATURE:
<223> OTHER INFORMATION: An additional sequence preceding the Kex2 site
```

```
in the expression cassette pALK1264, pALK1131 and pALK1134

<400> SEQUENCE: 22

Gly Gln Cys Gly Gly
1               5

<210> SEQ ID NO 23
<211> LENGTH: 6
<212> TYPE: PRT
<213> ORGANISM: Nonomuraea flexuosa
<220> FEATURE:
<223> OTHER INFORMATION: N-terminal sequence of mature Nf Xyn11A and
      recombinant Xyn11A polypeptides, named as r33.4 kDa, r23.8 kDa and
      r22.0 kDa

<400> SEQUENCE: 23

Asp Thr Thr Ile Thr Gln
1               5

<210> SEQ ID NO 24
<211> LENGTH: 6
<212> TYPE: DNA
<213> ORGANISM: Nonomuraea flexuosa
<220> FEATURE:
<223> OTHER INFORMATION: An NruI recognition site introduced into a Kex2
      linker

<400> SEQUENCE: 24 tcgcga                                                               6

<210> SEQ ID NO 25
<211> LENGTH: 12
<212> TYPE: DNA
<213> ORGANISM: Nonomuraea flexuosa
<220> FEATURE:
<223> OTHER INFORMATION: Kex2 linker which facilitates the construction
      of fusions

<400> SEQUENCE: 25
cgcgacaagc gc                                                       12
```